US012564408B2

(12) United States Patent
Guidotti et al.

(10) Patent No.: US 12,564,408 B2
(45) Date of Patent: Mar. 3, 2026

(54) MEDICAL OCCLUDER DELIVERY SYSTEMS

(71) Applicant: UNIVERSITAT ZURICH, Zurich (CH)

(72) Inventors: Andrea Guidotti, Schwerzenbach (CH); Boaz Harari, Ganey Tikva (IL); Luca Vicentini, Opfikon (CH); Pietro Gozzoli, Zurich (CH)

(73) Assignee: UNIVERSITAT ZURICH, Zurich (CH)

( * ) Notice: Subject to any disclaimer, the term of this patent is extended or adjusted under 35 U.S.C. 154(b) by 732 days.

(21) Appl. No.: 17/913,627

(22) PCT Filed: Mar. 25, 2021

(86) PCT No.: PCT/IB2021/052474
§ 371 (c)(1),
(2) Date: Sep. 22, 2022

(87) PCT Pub. No.: WO2021/191833
PCT Pub. Date: Sep. 30, 2021

(65) Prior Publication Data
US 2023/0146949 A1 May 11, 2023

Related U.S. Application Data

(60) Provisional application No. 62/994,465, filed on Mar. 25, 2020.

(51) Int. Cl.
A61B 17/12 (2006.01)
A61M 25/10 (2013.01)

(52) U.S. Cl.
CPC .. A61B 17/12136 (2013.01); A61B 17/12122 (2013.01); A61M 25/10182 (2013.11);
(Continued)

(58) Field of Classification Search
CPC ...... A61M 25/10182; A61M 25/10184; A61M 25/10; A61M 25/1036; A61M 2025/1054;
(Continued)

(56) References Cited

U.S. PATENT DOCUMENTS

| | | |
|---|---|---|
| 3,834,394 A | 9/1974 | Hunter et al. |
| 4,686,962 A | 8/1987 | Haber |

(Continued)

FOREIGN PATENT DOCUMENTS

| | | |
|---|---|---|
| CN | 104905890 A | 9/2015 |
| CN | 204971415 U | 1/2016 |

(Continued)

OTHER PUBLICATIONS

An International Search Report and a Written Opinion both dated Dec. 4, 2018, which issued during the prosecution of Applicant's PCT/EP2018/075716.

(Continued)

*Primary Examiner* — Katherine H Schwiker
*Assistant Examiner* — Lauren Dubose
(74) *Attorney, Agent, or Firm* — Sughrue Mion, PLLC

(57) ABSTRACT

A delivery system is provided for delivering and deploying an implantable balloon-based occlusion device including an inflatable balloon. The delivery system includes a handle including a plunger slidingly disposed in a fluid-retaining chamber, and a proximal rotatable user-control knob. A fluid-conveyance lumen catheter is shaped so as to define a catheter fluid-conveyance lumen in fluid communication with the fluid-retaining chamber and the inflatable balloon when the fluid-conveyance lumen catheter is coupled to the inflatable balloon. A catheter lumen shaft is configured to be in reversible connection with the balloon-based occlusion device, longitudinally slidable with respect to the handle. Rotation of the knob in a first rotational direction concur-
(Continued)

rently expels at least some of the fluid from the fluid-retaining chamber into the inflatable balloon, via the catheter fluid-conveyance lumen, and shortens a length of the balloon-based occlusion device by proximally pulling the catheter lumen shaft. Other embodiments are also described.

20 Claims, 19 Drawing Sheets

(52) U.S. Cl.
CPC .............. *A61B 2017/12095* (2013.01); *A61M 2025/1054* (2013.01); *A61M 2025/1068* (2013.01)

(58) Field of Classification Search
CPC ..... A61M 2025/1068; A61B 17/12172; A61B 17/12022; A61B 17/12145; A61B 2017/0038; A61B 2017/1205; A61B 2017/00592; A61B 2017/00597; A61B 2017/00623; A61B 2017/12054; A61B 2017/00619; A61B 2017/12095; A61B 2017/00557
See application file for complete search history.

(56) References Cited

U.S. PATENT DOCUMENTS

| | | | |
|---|---|---|---|
| 4,802,479 A | 2/1989 | Haber et al. |
| 5,411,475 A | 5/1995 | Atala et al. |
| 5,499,995 A | 3/1996 | Teirstein |
| 5,795,325 A | 8/1998 | Valley et al. |
| 5,830,228 A | 11/1998 | Knapp et al. |
| 5,853,422 A | 12/1998 | Huebsch et al. |
| 6,117,159 A | 9/2000 | Huebsch et al. |
| 6,174,322 B1 | 1/2001 | Schneidt |
| 6,231,561 B1 | 5/2001 | Frazier et al. |
| 6,267,747 B1 | 7/2001 | Samson et al. |
| 6,273,907 B1 | 8/2001 | Laufer |
| 6,290,674 B1 | 9/2001 | Roue et al. |
| 6,328,727 B1 | 12/2001 | Frazier et al. |
| 6,334,864 B1 | 1/2002 | Amplatz et al. |
| 6,419,669 B1 | 7/2002 | Frazier et al. |
| 6,440,097 B1 | 8/2002 | Kupiecki |
| 6,468,301 B1 | 10/2002 | Amplatz et al. |
| 6,468,303 B1 | 10/2002 | Amplatz et al. |
| 6,488,689 B1 | 12/2002 | Kaplan et al. |
| 6,537,300 B2 | 3/2003 | Girton |
| 6,544,268 B1 | 4/2003 | Lazarus |
| 6,551,303 B1 | 4/2003 | Van Tassel et al. |
| 6,638,257 B2 | 10/2003 | Amplatz |
| 6,652,555 B1 | 11/2003 | VanTassel et al. |
| 6,652,556 B1 | 11/2003 | VanTassel et al. |
| 6,656,488 B2 | 12/2003 | Yi et al. |
| 6,692,491 B1 | 2/2004 | Phan |
| 6,926,712 B2 | 8/2005 | Phan |
| 6,932,816 B2 | 8/2005 | Phan |
| 6,941,169 B2 | 9/2005 | Pappu |
| 6,942,661 B2 | 9/2005 | Swanson |
| 6,942,681 B2 | 9/2005 | Johnson |
| 6,964,669 B1 | 11/2005 | Knapp et al. |
| 6,970,742 B2 | 11/2005 | Mann et al. |
| 6,994,092 B2 | 2/2006 | Van Der et al. |
| 7,011,671 B2 | 3/2006 | Welch |
| 7,044,134 B2 | 5/2006 | Khairkhahan et al. |
| 7,056,294 B2 | 6/2006 | Khairkhahan et al. |
| 7,169,164 B2 | 1/2007 | Borillo et al. |
| 7,211,048 B1 | 5/2007 | Najafi et al. |
| 7,293,562 B2 | 11/2007 | Malecki et al. |
| 7,338,514 B2 | 3/2008 | Wahr et al. |
| 7,374,560 B2 | 5/2008 | Ressemann et al. |
| 7,470,282 B2 | 12/2008 | Shelso |
| 7,473,271 B2 | 1/2009 | Gunderson |
| 7,483,743 B2 | 1/2009 | Mann et al. |

| | | | |
|---|---|---|---|
| 7,549,988 B2 | 6/2009 | Eberl et al. |
| 7,597,704 B2 | 10/2009 | Frazier et al. |
| 7,604,612 B2 | 10/2009 | Ressemann et al. |
| 7,615,010 B1 | 11/2009 | Najafi et al. |
| 7,654,978 B2 | 2/2010 | Wahr et al. |
| 7,713,282 B2 | 5/2010 | Frazier et al. |
| 7,722,641 B2 | 5/2010 | Van Der Burg et al. |
| 7,735,493 B2 | 6/2010 | Van Der Burg et al. |
| 7,740,627 B2 | 6/2010 | Gammie et al. |
| 7,749,157 B2 | 7/2010 | Bertolero |
| 7,824,341 B2 | 11/2010 | Krishnan |
| 7,828,818 B2 | 11/2010 | Zang et al. |
| 7,837,619 B2 | 11/2010 | Sogard et al. |
| 7,846,168 B2 | 12/2010 | Liddicoat et al. |
| 7,846,175 B2 | 12/2010 | Bonnette et al. |
| 7,857,811 B2 | 12/2010 | Vaska et al. |
| 7,892,228 B2 | 2/2011 | Landis et al. |
| 7,918,865 B2 | 4/2011 | Liddicoat et al. |
| 7,972,359 B2 | 7/2011 | Kreidler |
| 7,976,564 B2 | 7/2011 | Blaeser et al. |
| 7,998,095 B2 | 8/2011 | McAuley |
| 7,998,138 B2 | 8/2011 | McAuley |
| 8,002,771 B2 | 8/2011 | Cox et al. |
| 8,034,061 B2 | 10/2011 | Amplatz et al. |
| 8,043,258 B2 | 10/2011 | Ostroot |
| 8,048,147 B2 | 11/2011 | Adams |
| 8,052,715 B2 | 11/2011 | Quinn et al. |
| 8,057,530 B2 | 11/2011 | Kusleika et al. |
| 8,080,032 B2 | 12/2011 | Van Der Burg et al. |
| 8,097,015 B2 | 1/2012 | Devellian |
| 8,100,938 B2 | 1/2012 | Figulla et al. |
| 8,108,069 B2 | 1/2012 | Stahler et al. |
| 8,114,123 B2 | 2/2012 | Brenzel et al. |
| 8,133,221 B2 | 3/2012 | Malecki et al. |
| 8,142,470 B2 | 3/2012 | Quinn et al. |
| 8,148,470 B1 | 4/2012 | Holtcamp et al. |
| 8,162,974 B2 | 4/2012 | Eskuri et al. |
| 8,163,004 B2 | 4/2012 | Amplatz et al. |
| 8,167,894 B2 | 5/2012 | Miles et al. |
| 8,167,905 B2 | 5/2012 | Michler et al. |
| 8,197,527 B2 | 6/2012 | Borillo et al. |
| 8,204,605 B2 | 6/2012 | Hastings et al. |
| 8,211,096 B2 | 7/2012 | Pless et al. |
| 8,221,348 B2 | 7/2012 | Hackett et al. |
| 8,221,405 B2 | 7/2012 | Whisenant et al. |
| 8,235,885 B2 | 8/2012 | Whisenant et al. |
| 8,235,988 B2 | 8/2012 | Davis et al. |
| 8,252,051 B2 | 8/2012 | Chau et al. |
| 8,257,724 B2 | 9/2012 | Cromack et al. |
| 8,257,725 B2 | 9/2012 | Cromack et al. |
| 8,308,798 B2 | 11/2012 | Pintor et al. |
| 8,313,505 B2 | 11/2012 | Amplatz et al. |
| 8,361,138 B2 | 1/2013 | Adams |
| 8,366,743 B2 | 2/2013 | Zeng et al. |
| 8,372,112 B2 | 2/2013 | Christianson et al. |
| 8,398,670 B2 | 3/2013 | Amplatz et al. |
| 8,402,974 B2 | 3/2013 | Davis et al. |
| 8,408,214 B2 | 4/2013 | Spenser |
| 8,409,219 B2 | 4/2013 | Kelley et al. |
| 8,463,359 B2 | 6/2013 | Saadat et al. |
| 8,480,708 B2 | 7/2013 | Kassab et al. |
| 8,491,649 B2 | 7/2013 | Mach |
| 8,511,214 B2 | 8/2013 | Gries |
| 8,523,897 B2 | 9/2013 | Van Der Burg et al. |
| 8,523,940 B2 | 9/2013 | Richardson et al. |
| 8,529,597 B2 | 9/2013 | Linder et al. |
| 8,540,616 B2 | 9/2013 | Whisenant et al. |
| 8,545,491 B2 | 10/2013 | Abboud et al. |
| 8,550,982 B2 | 10/2013 | Eby |
| 8,568,474 B2 | 10/2013 | Yeung et al. |
| 8,574,264 B2 | 11/2013 | Blaeser et al. |
| 8,613,765 B2 | 12/2013 | Bonhoeffer et al. |
| 8,617,145 B2 | 12/2013 | Longoria |
| 8,621,975 B2 | 1/2014 | Russo et al. |
| 8,636,764 B2 | 1/2014 | Miles et al. |
| 8,647,361 B2 | 2/2014 | Borillo et al. |
| 8,647,367 B2 | 2/2014 | Kassab et al. |
| 8,652,201 B2 | 2/2014 | Oberti et al. |
| 8,663,245 B2 | 3/2014 | Francischelli et al. |

(56)            References Cited

U.S. PATENT DOCUMENTS

| | | |
|---|---|---|
| 8,673,001 B2 | 3/2014 | Cartledge et al. |
| 8,690,911 B2 | 4/2014 | Miles et al. |
| 8,696,742 B2 | 4/2014 | Pintor et al. |
| 8,709,007 B2 | 4/2014 | Vaska |
| 8,715,270 B2 | 5/2014 | Weitzner et al. |
| 8,721,636 B2 | 5/2014 | Vaska et al. |
| 8,740,934 B2 | 6/2014 | McGuckin, Jr. |
| 8,747,297 B2 | 6/2014 | Miyoshi et al. |
| 8,747,453 B2 | 6/2014 | Amplatz et al. |
| 8,747,462 B2 | 6/2014 | Hill et al. |
| 8,758,294 B2 | 6/2014 | Kim et al. |
| 8,758,372 B2 | 6/2014 | Cartledge et al. |
| 8,758,389 B2 | 6/2014 | Glimsdale |
| 8,764,787 B2 | 7/2014 | Ren |
| 8,764,793 B2 | 7/2014 | Lee |
| 8,771,297 B2 | 7/2014 | Miller et al. |
| 8,777,974 B2 | 7/2014 | Amplatz et al. |
| 8,778,008 B2 | 7/2014 | Amplatz et al. |
| 8,784,469 B2 | 7/2014 | Kassab |
| 8,795,310 B2 | 8/2014 | Fung et al. |
| 8,795,328 B2 | 8/2014 | Miles et al. |
| 8,801,706 B2 | 8/2014 | Rothstein et al. |
| 8,801,746 B1 | 8/2014 | Kreidler et al. |
| 8,808,371 B2 | 8/2014 | Cartledge |
| 8,814,778 B2 | 8/2014 | Kiser et al. |
| D713,527 S | 9/2014 | Heipl |
| 8,821,529 B2 | 9/2014 | Kariniemi et al. |
| 8,834,519 B2 | 9/2014 | Van Der Burg et al. |
| 8,840,641 B2 | 9/2014 | Miles et al. |
| 8,840,655 B2 | 9/2014 | Edmiston et al. |
| 8,845,711 B2 | 9/2014 | Miles et al. |
| 8,864,809 B2 | 10/2014 | Miles et al. |
| 8,864,823 B2 | 10/2014 | Cartledge et al. |
| 8,876,776 B2 | 11/2014 | Kassab et al. |
| 8,880,185 B2 | 11/2014 | Hastings et al. |
| 8,882,830 B2 | 11/2014 | Cartledge et al. |
| 8,900,287 B2 | 12/2014 | Amplatz et al. |
| 8,915,958 B2 | 12/2014 | Braido |
| 8,940,015 B2 | 1/2015 | Kariniemi |
| 8,951,251 B2 | 2/2015 | Willard |
| 8,956,304 B2 | 2/2015 | Schecter |
| 8,974,451 B2 | 3/2015 | Smith |
| 8,979,941 B2 | 3/2015 | Davis et al. |
| 8,986,375 B2 | 3/2015 | Garde et al. |
| D727,500 S | 4/2015 | Heipl |
| D727,501 S | 4/2015 | Heipl |
| D728,102 S | 4/2015 | Heipl |
| 9,011,551 B2 | 4/2015 | Oral et al. |
| 9,017,375 B2 | 4/2015 | Thommen |
| 9,023,034 B2 | 5/2015 | Jenson et al. |
| 9,028,485 B2 | 5/2015 | Edmunds et al. |
| 9,034,006 B2 | 5/2015 | Quinn et al. |
| 9,039,724 B2 | 5/2015 | Amplatz et al. |
| 9,039,752 B2 | 5/2015 | Russo et al. |
| 9,050,106 B2 | 6/2015 | Hill et al. |
| 9,055,933 B2 | 6/2015 | Escobar et al. |
| 9,055,959 B2 | 6/2015 | Vaska et al. |
| 9,060,761 B2 | 6/2015 | Hastings et al. |
| 9,066,710 B2 | 6/2015 | Dale et al. |
| 9,066,826 B2 | 6/2015 | Heidner et al. |
| 9,072,602 B2 | 7/2015 | Glozman et al. |
| 9,072,604 B1 | 7/2015 | Melnick et al. |
| 9,079,000 B2 | 7/2015 | Hanson et al. |
| 9,084,589 B2 | 7/2015 | Moszner |
| 9,084,609 B2 | 7/2015 | Smith |
| 9,084,621 B2 | 7/2015 | Weitzner et al. |
| 9,089,350 B2 | 7/2015 | Willard |
| 9,089,414 B2 | 7/2015 | Zimmerman et al. |
| 9,107,750 B2 | 8/2015 | Cartledge et al. |
| 9,113,890 B2 | 8/2015 | Dasnurkar et al. |
| 9,119,600 B2 | 9/2015 | Richardson et al. |
| 9,119,632 B2 | 9/2015 | Jenson et al. |
| 9,125,653 B2 | 9/2015 | Kovach |
| 9,131,932 B2 | 9/2015 | Tegels |
| 9,132,007 B2 | 9/2015 | Menk et al. |
| 9,138,208 B2 | 9/2015 | Linder et al. |
| 9,144,431 B2 | 9/2015 | Friedman et al. |
| 9,144,663 B2 | 9/2015 | Ahlberg et al. |
| 9,155,589 B2 | 10/2015 | Jenson |
| 9,161,758 B2 | 10/2015 | Figulla et al. |
| 9,162,046 B2 | 10/2015 | Hill et al. |
| 9,173,696 B2 | 11/2015 | Schauer et al. |
| 9,186,174 B2 | 11/2015 | Krishnan |
| 9,186,209 B2 | 11/2015 | Weber et al. |
| 9,186,210 B2 | 11/2015 | Jenson |
| 9,186,211 B2 | 11/2015 | Mathur |
| 9,192,435 B2 | 11/2015 | Jenson |
| 9,192,790 B2 | 11/2015 | Hastings et al. |
| 9,198,683 B2 | 12/2015 | Friedman et al. |
| 9,216,014 B2 | 12/2015 | Devellian et al. |
| 9,220,402 B2 | 12/2015 | Rothe et al. |
| 9,220,487 B2 | 12/2015 | Davis et al. |
| 9,220,558 B2 | 12/2015 | Willard |
| 9,220,561 B2 | 12/2015 | Crow et al. |
| 9,226,838 B2 | 1/2016 | Wang et al. |
| 9,232,992 B2 | 1/2016 | Heidner et al. |
| 9,241,792 B2 | 1/2016 | Benichou et al. |
| 9,254,141 B2 | 2/2016 | Morris et al. |
| 9,254,192 B2 | 2/2016 | Lutter et al. |
| 9,271,736 B2 | 3/2016 | Heipl |
| 9,277,905 B2 | 3/2016 | Cully et al. |
| 9,277,915 B2 | 3/2016 | Belson et al. |
| 9,289,266 B2 | 3/2016 | Weitzner et al. |
| 9,290,612 B2 | 3/2016 | Martin et al. |
| 9,295,472 B2 | 3/2016 | Ottma |
| 9,295,484 B2 | 3/2016 | Solem |
| 9,297,845 B2 | 3/2016 | Mathur |
| 9,301,838 B2 | 4/2016 | Kapadia |
| 9,307,999 B2 | 4/2016 | Li et al. |
| 9,320,525 B2 | 4/2016 | Khieu et al. |
| 9,326,751 B2 | 5/2016 | Hastings |
| 9,326,852 B2 | 5/2016 | Spenser |
| 9,333,073 B2 | 5/2016 | Quadri et al. |
| 9,339,274 B2 | 5/2016 | Dakin |
| 9,345,462 B2 | 5/2016 | Weitzner et al. |
| 9,351,716 B2 | 5/2016 | Miles et al. |
| 9,358,365 B2 | 6/2016 | Smith et al. |
| 9,364,284 B2 | 6/2016 | Groff et al. |
| 9,370,418 B2 | 6/2016 | Pintor et al. |
| 9,375,209 B2 | 6/2016 | Akpinar |
| 9,375,218 B2 | 6/2016 | Wheeler et al. |
| 9,398,951 B2 | 7/2016 | Alkhatib et al. |
| 9,408,608 B2 | 8/2016 | Clark, III et al. |
| 9,408,661 B2 | 8/2016 | Haverkost |
| 9,408,951 B2 | 8/2016 | Larsen et al. |
| 9,414,842 B2 | 8/2016 | Glimsdale et al. |
| 9,420,955 B2 | 8/2016 | Weber |
| 9,421,071 B2 | 8/2016 | Smith et al. |
| 9,427,215 B2 | 8/2016 | Cartledge et al. |
| 9,427,235 B2 | 8/2016 | Krishnan |
| 9,427,550 B2 | 8/2016 | Dakin et al. |
| 9,433,760 B2 | 9/2016 | Subramaniam et al. |
| 9,445,798 B2 | 9/2016 | Amplatz et al. |
| 9,445,799 B2 | 9/2016 | Amplatz et al. |
| 9,456,877 B2 | 10/2016 | Weitzner et al. |
| 9,456,897 B2 | 10/2016 | Krivoruchko et al. |
| 9,463,024 B2 | 10/2016 | Kiser et al. |
| 9,463,062 B2 | 10/2016 | Smith et al. |
| 9,468,437 B2 | 10/2016 | Michler et al. |
| 9,474,516 B2 | 10/2016 | Clark et al. |
| 9,474,598 B2 | 10/2016 | Gregg et al. |
| 9,474,599 B2 | 10/2016 | Keränen |
| 9,492,156 B2 | 11/2016 | Tegels |
| 9,492,276 B2 | 11/2016 | Lee et al. |
| 9,492,623 B2 | 11/2016 | Kapadia et al. |
| 9,498,206 B2 | 11/2016 | Fung et al. |
| 9,498,228 B2 | 11/2016 | Dale et al. |
| 9,510,811 B2 | 12/2016 | Akpinar |
| 9,532,772 B2 | 1/2017 | Moszner et al. |
| 9,545,306 B2 | 1/2017 | Tabor |
| 9,572,583 B2 | 2/2017 | Kauphusman et al. |
| 9,579,030 B2 | 2/2017 | Scheuermann et al. |
| 9,579,194 B2 | 2/2017 | Elizondo et al. |
| 9,585,643 B2 | 3/2017 | Terwey |

(56) References Cited

U.S. PATENT DOCUMENTS

| | | | |
|---|---|---|---|
| 9,585,644 | B2 | 3/2017 | Linder et al. |
| 9,610,082 | B2 | 4/2017 | Morris et al. |
| 9,622,133 | B1 | 4/2017 | Guvenc |
| 9,636,222 | B2 | 5/2017 | Oslund |
| 9,642,706 | B2 | 5/2017 | Eidenschink |
| 9,649,115 | B2 | 5/2017 | Edmiston et al. |
| 9,649,156 | B2 | 5/2017 | Jenson et al. |
| 9,650,730 | B2 | 5/2017 | Heipl et al. |
| 9,655,606 | B2 | 5/2017 | Le |
| 9,662,205 | B2 | 5/2017 | Eidenschink |
| 9,668,811 | B2 | 6/2017 | Sogard et al. |
| 9,668,856 | B2 | 6/2017 | Para |
| 9,668,857 | B2 | 6/2017 | Braido et al. |
| 9,668,858 | B2 | 6/2017 | Morin et al. |
| 9,675,451 | B2 | 6/2017 | Garde et al. |
| 9,681,861 | B2 | 6/2017 | Heisel et al. |
| 9,687,166 | B2 | 6/2017 | Subramaniam et al. |
| 9,687,341 | B2 | 6/2017 | Alkhatib et al. |
| 9,687,585 | B2 | 6/2017 | Bernasconi et al. |
| 9,693,781 | B2 | 7/2017 | Miles et al. |
| 9,693,821 | B2 | 7/2017 | Hanson et al. |
| 9,694,115 | B2 | 7/2017 | Zhang et al. |
| 9,700,323 | B2 | 7/2017 | Clark |
| 9,707,036 | B2 | 7/2017 | Anderson et al. |
| 9,713,730 | B2 | 7/2017 | Mathur et al. |
| 9,717,501 | B2 | 8/2017 | Kauphusman et al. |
| 9,730,701 | B2 | 8/2017 | Tischler et al. |
| 9,737,309 | B1 | 8/2017 | Ad |
| 9,750,605 | B2 | 9/2017 | Ganesan et al. |
| 9,757,230 | B2 | 9/2017 | Fahim et al. |
| 9,770,606 | B2 | 9/2017 | Pikus et al. |
| 9,775,533 | B2 | 10/2017 | Ong et al. |
| 9,789,232 | B2 | 10/2017 | Liu et al. |
| 9,795,387 | B2 | 10/2017 | Miles et al. |
| 9,795,481 | B2 | 10/2017 | Callas et al. |
| 9,795,765 | B2 | 10/2017 | Romoscanu |
| 9,808,253 | B2 | 11/2017 | Li et al. |
| 9,808,300 | B2 | 11/2017 | Hastings et al. |
| 9,808,311 | B2 | 11/2017 | Wang et al. |
| 9,820,851 | B2 | 11/2017 | Braido |
| 9,820,852 | B2 | 11/2017 | Braido et al. |
| 9,827,039 | B2 | 11/2017 | Dandler et al. |
| 9,833,283 | B2 | 12/2017 | Hanson et al. |
| 9,839,430 | B2 | 12/2017 | Willems et al. |
| 9,839,431 | B2 | 12/2017 | Meyer et al. |
| 9,844,453 | B2 | 12/2017 | Stack et al. |
| 9,848,898 | B2 | 12/2017 | Friedman et al. |
| 9,848,976 | B2 | 12/2017 | Angel et al. |
| 9,848,981 | B2 | 12/2017 | Suri et al. |
| 9,863,031 | B2 | 1/2018 | Zhang et al. |
| 9,867,697 | B2 | 1/2018 | Alkhatib et al. |
| 9,877,710 | B2 | 1/2018 | Amplatz et al. |
| 9,877,726 | B2 | 1/2018 | Liu et al. |
| 9,878,072 | B2 | 1/2018 | Zhang et al. |
| 9,883,855 | B2 | 2/2018 | Tegels et al. |
| 9,883,936 | B2 | 2/2018 | Sutton et al. |
| 9,888,926 | B2 | 2/2018 | Phan et al. |
| 9,889,004 | B2 | 2/2018 | Braido |
| 9,895,194 | B2 | 2/2018 | Anderson et al. |
| 9,901,443 | B2 | 2/2018 | Morriss et al. |
| 9,907,609 | B2 | 3/2018 | Cao et al. |
| 9,913,652 | B2 | 3/2018 | Bridgeman et al. |
| 9,913,715 | B2 | 3/2018 | Braido et al. |
| 9,918,707 | B2 | 3/2018 | Zhuang |
| 9,919,080 | B1 | 3/2018 | Chen et al. |
| 9,925,001 | B2 | 3/2018 | Willard et al. |
| 9,931,204 | B2 | 4/2018 | Rothstein et al. |
| 9,936,956 | B2 | 4/2018 | Fung et al. |
| 9,943,315 | B2 | 4/2018 | Kaplan et al. |
| 9,943,365 | B2 | 4/2018 | Haverkost et al. |
| 9,949,825 | B2 | 4/2018 | Braido et al. |
| 9,955,971 | B2 | 5/2018 | Xu et al. |
| 9,956,033 | B2 | 5/2018 | Squire et al. |
| 9,962,223 | B2 | 5/2018 | Lindquist et al. |
| 9,974,649 | B2 | 5/2018 | Racchini et al. |
| 9,980,818 | B2 | 5/2018 | Chau et al. |
| 9,993,234 | B2 | 6/2018 | Maslanka et al. |
| 10,010,402 | B2 | 7/2018 | Wang et al. |
| 10,013,082 | B2 | 7/2018 | Schecter |
| 10,016,200 | B2 | 7/2018 | Tegels |
| 10,022,182 | B2 | 7/2018 | Willard et al. |
| 10,028,746 | B2 | 7/2018 | Prom |
| 10,034,748 | B2 | 7/2018 | Tseng et al. |
| 10,045,784 | B2 | 8/2018 | Friedman et al. |
| 10,052,168 | B2 | 8/2018 | Krishnan |
| 10,058,348 | B2 | 8/2018 | Morris et al. |
| 10,058,636 | B2 | 8/2018 | Xie et al. |
| 10,058,639 | B2 | 8/2018 | Zhang et al. |
| 10,064,612 | B2 | 9/2018 | Malakan Rad et al. |
| 10,064,628 | B2 | 9/2018 | Edmiston et al. |
| 10,076,330 | B2 | 9/2018 | Sander et al. |
| 10,076,335 | B2 | 9/2018 | Zaver et al. |
| 10,085,799 | B2 | 10/2018 | Smith |
| 10,098,640 | B2 | 10/2018 | Bertolero et al. |
| 10,105,219 | B2 | 10/2018 | Kovach |
| 10,117,743 | B2 | 11/2018 | Kumar et al. |
| 10,130,369 | B2 | 11/2018 | Fung et al. |
| 10,130,467 | B2 | 11/2018 | Braido et al. |
| 10,143,478 | B2 | 12/2018 | Forbes |
| 10,143,551 | B2 | 12/2018 | Braido et al. |
| 10,271,949 | B2 | 4/2019 | Dakin et al. |
| 2003/0191516 | A1 | 10/2003 | Weldon et al. |
| 2003/0220667 | A1 | 11/2003 | Van Der Burg et al. |
| 2004/0098017 | A1 | 5/2004 | Saab et al. |
| 2004/0254594 | A1 | 12/2004 | Alfaro |
| 2005/0288706 | A1 | 12/2005 | Widomski et al. |
| 2006/0004442 | A1 | 1/2006 | Spenser et al. |
| 2006/0200191 | A1 | 9/2006 | Zadno-azizi et al. |
| 2007/0135831 | A1 | 6/2007 | Burnett |
| 2007/0225756 | A1 | 9/2007 | Preinitz et al. |
| 2008/0071310 | A1 | 3/2008 | Hoffman et al. |
| 2008/0103479 | A1 | 5/2008 | Cheng et al. |
| 2010/0125244 | A1 | 5/2010 | Mcandrew |
| 2010/0185233 | A1 | 7/2010 | Thommen |
| 2011/0125132 | A1* | 5/2011 | Krolik ............ A61M 25/10185 604/509 |
| 2011/0172697 | A1 | 7/2011 | Jönsson |
| 2012/0078295 | A1 | 3/2012 | Steiner et al. |
| 2012/0323270 | A1 | 12/2012 | Lee |
| 2013/0030519 | A1 | 1/2013 | Tran et al. |
| 2013/0211495 | A1 | 8/2013 | Halden et al. |
| 2014/0100596 | A1 | 4/2014 | Rudman et al. |
| 2014/0257457 | A1 | 9/2014 | Glazier et al. |
| 2014/0277426 | A1 | 9/2014 | Dakin et al. |
| 2016/0045165 | A1 | 2/2016 | Braido et al. |
| 2018/0008248 | A1 | 1/2018 | Rafiee et al. |
| 2018/0161039 | A1 | 6/2018 | Harks |
| 2019/0076638 | A1* | 3/2019 | Dailey ............ A61M 25/10182 |
| 2020/0054343 | A1 | 2/2020 | Min et al. |
| 2020/0107836 | A1 | 4/2020 | O'halloran et al. |
| 2020/0275935 | A1 | 9/2020 | Maisano et al. |
| 2020/0305887 | A1 | 10/2020 | Lashinski et al. |
| 2021/0298728 | A1 | 9/2021 | Lashinski et al. |
| 2021/0386429 | A1 | 12/2021 | Franano et al. |
| 2022/0022854 | A1 | 1/2022 | Lashinski et al. |
| 2022/0087741 | A1 | 3/2022 | Lashinski et al. |

FOREIGN PATENT DOCUMENTS

| | | | |
|---|---|---|---|
| CN | 106344082 | A | 1/2017 |
| EP | 1651117 | | 1/2007 |
| EP | 1113751 | | 3/2007 |
| EP | 1154723 | | 12/2007 |
| EP | 1891902 | | 2/2008 |
| EP | 1788957 | | 3/2008 |
| EP | 1 974 685 | A1 | 10/2008 |
| EP | 1881804 | | 9/2009 |
| EP | 1313406 | | 6/2010 |
| EP | 1123130 | | 7/2010 |
| EP | 1948030 | | 7/2010 |
| EP | 1441649 | | 8/2011 |
| EP | 1993621 | | 8/2011 |
| EP | 1842490 | | 9/2011 |
| EP | 2074953 | | 6/2012 |

(56)         References Cited

FOREIGN PATENT DOCUMENTS

| | | | |
|---|---|---|---|
| EP | 2019633 | | 8/2012 |
| EP | 2248471 | | 10/2012 |
| EP | 1575421 | | 10/2013 |
| EP | 2327429 | | 9/2014 |
| EP | 1761296 | | 11/2014 |
| EP | 1765225 | | 9/2015 |
| EP | 2630919 | | 9/2015 |
| EP | 2822656 | | 10/2016 |
| EP | 2872051 | | 3/2017 |
| EP | 2970572 | | 4/2017 |
| EP | 2779910 | | 5/2017 |
| EP | 2967852 | | 6/2017 |
| EP | 3037043 | | 9/2017 |
| EP | 2617386 | | 10/2017 |
| EP | 2819585 | | 11/2017 |
| EP | 3043746 | | 11/2017 |
| EP | 3183012 | | 12/2017 |
| EP | 1768604 | | 1/2018 |
| EP | 2967869 | | 1/2018 |
| EP | 3125780 | | 1/2018 |
| EP | 3044221 | | 2/2018 |
| EP | 2575678 | | 5/2018 |
| EP | 2833836 | | 5/2018 |
| EP | 2908744 | | 8/2018 |
| EP | 2918251 | | 8/2018 |
| EP | 3193791 | | 8/2018 |
| EP | 2753246 | | 11/2018 |
| EP | 3010446 | | 12/2018 |
| EP | 3459469 | | 3/2019 |
| EP | 3 620 134 | A1 | 3/2020 |
| WO | 95/032018 | | 11/1995 |
| WO | 1999/018886 | | 4/1999 |
| WO | 2000/012169 | | 3/2000 |
| WO | 03/039624 | A2 | 5/2003 |
| WO | 2005/092204 | A2 | 10/2005 |
| WO | 2011/011765 | A2 | 1/2011 |
| WO | 2013/068466 | | 5/2013 |
| WO | 2014/085590 | A1 | 6/2014 |
| WO | 2016/149653 | A2 | 9/2016 |
| WO | 2017/079234 | | 5/2017 |
| WO | 2017/161283 | | 9/2017 |

OTHER PUBLICATIONS

An International Search Report and a Written Opinion both dated Jun. 18, 2019, which issued during the prosecution of Applicant's PCT/US2019/024065.

An International Search Report and a Written Opinion both dated Jul. 6, 2021, which issued during the prosecution of Applicant's PCT/IB2021/052474.

An International Search Report and a Written Opinion both dated Mar. 29, 2021 which issued during the prosecution of Applicant's PCT/IL2020/051041.

European Search Report dated Mar. 12, 2018 which issued during the prosecution of Applicant's European App No. 17192792.4.

An Office Action dated Mar. 7, 2022, which issued during the prosecution of Indian Patent Application No. 202017015683.

An Office Action dated Dec. 22, 2021, which issued during the prosecution of U.S. Appl. No. 16/649,777.

Notice of Allowance issued in United States Office Action issued Jun. 24, 2022 in U.S. Appl. No. 16/649,777.

Japanese Office Action issued Sep. 27, 2022 in Application No. 516870/2020.

Extended European Search Report issued Dec. 15, 2022 in Application No. 19862977.6.

Indian First Examination Report issued Feb. 3, 2023 in Application No. 202117016867.

Japanese Office Action issued Feb. 14, 2023 in Application No. 516654/2021.

Chinese Office Action issued Feb. 23, 2023 in Application No. 201880061656.0.

Japanese Decision of Refusal issued Jul. 11, 2023 in Application No. 516870/2020.

Chinese Office Action issued Oct. 18, 2023 in Application No. 201880061656.0.

United States Notice of Allowance issued Dec. 5, 2023 in U.S. Appl. No. 17/763,485.

Chinese Office Action issued Jan. 31, 2024 in Application No. 201980072797.7.

Japanese Office Action issued Mar. 12, 2024 in Application No. 2022-519406.

United States Non-Final Rejection issued May 22, 2023 in U.S. Appl. No. 17/763,485.

* cited by examiner

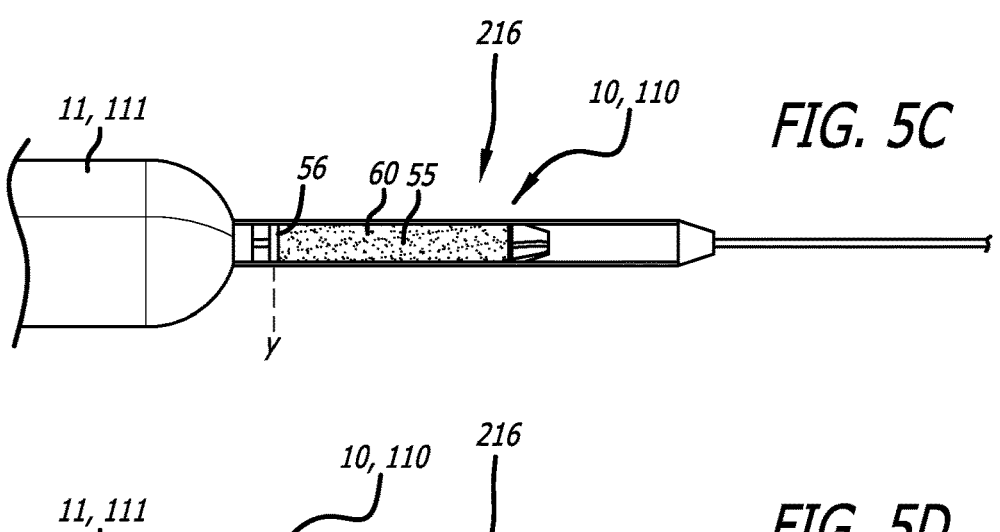
FIG. 5C
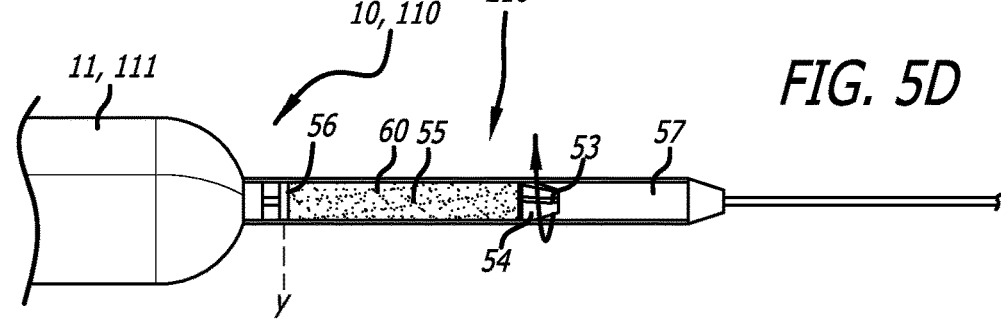
FIG. 5D
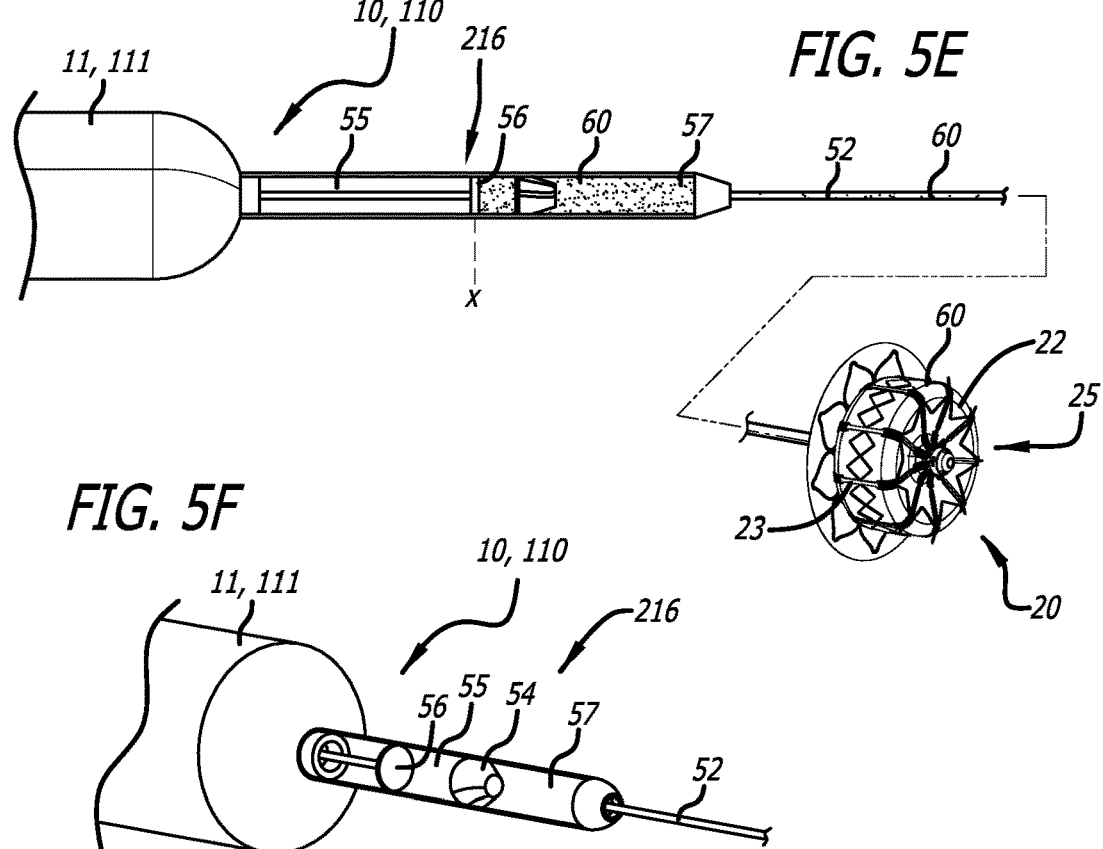
FIG. 5E
FIG. 5F

MEDICAL OCCLUDER DELIVERY SYSTEMS

CROSS-REFERENCE TO RELATED APPLICATIONS

The present patent application is the U.S. national stage of International Application PCT/IB2021/052474, filed Mar. 25, 2021, which claims priority from U.S. Provisional Application 62/994,465, filed Mar. 25, 2020, which is assigned to the assignee of the present application and incorporated herein by reference.

FIELD OF THE APPLICATION

The present application relates generally to medical device systems and methods, that employ a catheter delivery systems or other device and liquid inflation lumens.

BACKGROUND OF THE APPLICATION

There are several types of pathologic passageways within the body. If located in blood vessels or in the heart, such passageways can cause alteration of blood flow. Paravalvular leak is a common complication of patients undergoing implantation of either surgical or transcatheter prostheses. The left atrial appendage (LAA) is a cavity that presents in the left atrium of the heart. In patients with atrial fibrillation the passage and steadiness of blood within this cavity can cause thrombus formation, which increase the risk of stroke. The option to treat these defects percutaneously may offers safer solution for high-risk patients, without exposing them to risk related to open heart reoperation. New concepts and implementations of occlusion devices based on detachable balloon implants are being developed, which are specifically designed for paravalvular leak occlusion, LAA occlusion or other irregular cardiovascular defects target sites.

The delivery of these new occlusion devices requires transcatheter methods and techniques using elongated catheter tools to target and position the devices at the desired implantation area in the subject's body.

The delivery of a balloon-based implant to a desired target site requires the performance of several steps, including navigation, trajectory, inflation, deflation, activation, dislocation, deployment and retrieval of the implant. Various systems have been developed for the delivery of balloon implants to a desired target site, which may be able to perform some or all of these required steps, usually by mean of handle controls, knobs or manipulation during the procedure by the operator. Some of these steps should be performed in combination among them, for a proper implant deployment, but the activation of them by the operator is sometimes not reliable, stable and efficient.

SUMMARY OF THE APPLICATION

Some embodiments of the present invention provide a delivery system for controlling the inflation, deflation, activation and deployment of a detachable balloon-based implant in medical procedures involving blood vessels, body cavities, cardiovascular defects occlusion, treatment of left atrial appendage, and the like.

In some applications of the present invention, a delivery system is provided for the control and deployment of a cardiovascular device, for occluding a cardiovascular defect or a gap between a medical device and adjacent body tissue. The delivery system is for use with a guidewire and a balloon-based occlusion device. The delivery system enables over-the-wire engagement of the cardiovascular defect, the adjustment of the length and orientation of the occlusion devices during deployment, and the inflation of the balloon chamber with saline or another filling fluid. The delivery system automates the balloon-based implant inflation and its shortening to the deployment configuration The delivery system comprises a fluid-retaining chamber, which is delimited by a tubular barrel having a proximal end, a distal end, and an internal surface. A plunger is slidingly disposed in the fluid-retaining chamber, as a movable membrane to draw fluid into the fluid-retaining chamber and expel fluid out of the fluid-retaining chamber, thereby filling and unfilling the fluid-retaining chamber, respectively. The fluid-retaining chamber includes a port at a distal end of the fluid-retaining chamber. The port is optionally connected to a cannular extension tube which is in fluid flow communication with the fluid-retaining chamber. The cannular extension may be used during or after the activation of the plunger into the fluid-retaining chamber to insert additional fluid into the fluid-retaining chamber and consequently into the balloon-based implant. The fluid-retaining chamber is configured to expel fluid to an catheter fluid-conveyance lumen connected proximally to the fluid-retaining chamber and distally coupled to the balloon-based implant. The expulsion of fluid from the fluid-retaining chamber inflates a balloon of the balloon-based implant during its deployment.

For some applications, the delivery system further comprises an actuator disposed longitudinally slidable in a delivery handle, in series to the fluid-retaining chamber, connected to a catheter lumen shaft which is in direct connection with the balloon-based implant throughout all the handle components and the catheter shaft which is connected to the implant. The actuator is longitudinally movable with respect to the delivery handle components so as to shorten or elongate a length of the implant.

For some applications, the delivery handle further comprises a double-threaded tube which connects and couples the actuation of the plunger into the fluid-retaining chamber and the longitudinal sliding of the actuator, automating the expulsion of fluid from the fluid-retaining chamber into the balloon-based implant, the withdrawing of fluid into the fluid-retaining chamber from the balloon-based implant, and the concurrent shortening or elongation, respectively, of the implant length. The double-threaded tube is activated by the rotation of a proximal rotatable user-control knob of the delivery handle.

In some applications of the present invention, the delivery handle further comprises a fluid-retaining chamber sliding mechanism which allows the movement of the fluid-retaining chamber over the plunger independently from the double-threaded tube. The fluid sliding chamber is actuated by a proximal rotatable user-control knob positioned the delivery handle.

In some applications of the present invention, the delivery handle further comprises a locking toggle mechanism which limits the movement of the double-threaded tube within a pre-fixed motion range. The locking toggle mechanism, when released, allows the prosecution of double-threaded tube movement until its full range of motion. The locking toggle mechanism is activated by a mechanical motion of a toggling button positioned on the delivery handle.

The delivery system thus provides for more reliable, stable, efficient, and simple delivery of inflatable balloon-based implants, automating some or all of the deployment steps performed manually in conventional deployment systems. The delivery system thus may reduce occurrence of misuse and other operator related implantation errors, and may reduce the overall procedure time required, and therefore reduce patient discomfort and improve precision and procedural outcomes. The delivery system may also reduce the amount of effort required by the physician prior to and during use of the system, as well as ensure that the balloon-based implant is properly implanted and maneuvered during insertion into the target tissue, during inflation of the balloon of the balloon-based implant, and during its deployment.

The device may further comprise a guidewire/infusion lumen disposed parallel to the catheter fluid-conveyance lumen, such as within catheter fluid-conveyance lumen. The guidewire/infusion lumen is also in fluid communication with the internal channel of the inflatable balloon, and may be used for wires, guidewires or fluid agent passage from the proximal end of the delivery handle, to the distal end of the balloon-based implant. The guidewire may be placed at the beginning of the delivery procedure, to guide the catheter to the target area. The agent delivered through this guidewire/infusion lumen may be used for fluoroscopic contrast fluid injection to the distal outlet of the balloon-based implant, outside of the balloon-based implant, as the balloon inflates. Such a configuration may be advantageous to evaluate the adherence of the balloon-based implant to the surrounding target anatomy, in order for the operator to evaluate if to further inflate the balloon-based implant in order to achieve complete adherence to the anatomy. A syringe may be used for the agent insertion into this guidewire/infusion lumen.

The delivery system may further comprise a micro-pump in fluid communication with the extension cannula to provide controlled balloon inflation without shortening of the implant. Alternatively, the micro-pump may be in communication with the fluid-retaining chamber, in order to activate the sliding movement of the chamber plunger and the activation of the coupled thread mechanism; such a configuration may be desirable to provide consistency in dose rates, amounts, and pressures, as well in device shortening, with limited operator interaction.

In another application of the present invention, a method is provided for inflating a balloon-based implant using blood from the patient during an implantation procedure, which is collected distally within the catheter and proximally to the implant.

The catheter system is provided with a delivery catheter connected to the balloon-based implant. The delivery catheter is shaped so as to define a fluid-retaining chamber within its lumen. A fluid passage hole is configured within this fluid-retaining chamber, passing through the shaft and in direct communication with the blood stream. A plunger is disposed within this fluid-retaining chamber, able to slide longitudinally using a delivery handle. Retracting the plunger proximally draws blood into this fluid-retaining chamber. Once the fluid-retaining chamber is full with the patient blood, the fluid-retaining chamber is circumferentially rotated to align its fluid passage hole to the connecting entrance of the fluid inflation catheter within the shaft, which is connected to the balloon-based implant. Once the fluid communication between the fluid-retaining chamber and the inflation catheter is completed, the plunger may be distally moved to provide inflation to the balloon-based implant.

These steps are reversible and may be used for deflating the balloon-based implant. These steps may be performed also more than once in series, to provide more inflation volume to the balloon-based implant.

This other application of the present invention may be combined with the other applications of the present invention described above.

There is therefore provided, in accordance with an application of the present invention, a delivery system for delivering and deploying an implantable balloon-based occlusion device that includes an inflatable balloon, the delivery system including:

a fluid-retaining chamber, delimited by a tubular barrel having a proximal end, a distal end, and an internal surface;

a plunger, which is slidingly disposed in the fluid-retaining chamber so as to provide a movable membrane configured to draw fluid into the fluid-retaining chamber and expel the fluid from the fluid-retaining chamber, thereby filling and unfilling the fluid-retaining chamber, respectively;

a delivery handle, which includes a proximal rotatable user-control knob;

a fluid-conveyance lumen catheter, which is shaped so as to define a catheter fluid-conveyance lumen in fluid communication (a) with the fluid-retaining chamber and (b) with the inflatable balloon of the balloon-based occlusion device when the fluid-conveyance lumen catheter is coupled to the inflatable balloon;

a catheter lumen shaft, which is in direct reversible connection with the balloon-based occlusion device, longitudinally slidable with respect to the delivery handle to set a shortening or elongation of a longitudinal dimension of the balloon-based occlusion device;

an actuator, connected to the catheter lumen shaft; and a double-threaded tube, which is connected to the proximal rotatable user-control knob, and which connects and couples actuation of the plunger into the fluid-retaining chamber and longitudinal sliding of the actuator, such that rotation of the proximal rotatable user-control knob:

in a first rotational direction, activates the double-threaded tube to concurrently (a) expel at least some of the fluid from the fluid-retaining chamber into the inflatable balloon of the balloon-based occlusion device, via the catheter fluid-conveyance lumen, and (b) shorten a length of the balloon-based occlusion device by proximally moving the actuator, which in turn proximally pulls the catheter lumen shaft, and in a second rotational direction opposite the first rotational direction, activates the double-threaded tube to concurrently (a) withdraw at least some of the fluid into the fluid-retaining chamber from the inflatable balloon of the balloon-based occlusion device, via the catheter fluid-conveyance lumen, and (b) elongate the length of the balloon-based occlusion device by distally moving the actuator, which in turn distally pushes the catheter lumen shaft.

For some applications, the catheter lumen shaft is disposed within the catheter fluid-conveyance lumen of the fluid-conveyance lumen catheter.

For some applications, the fluid-retaining chamber is disposed within the delivery handle.

For some applications, the delivery handle includes a delivery-handle fluid-conveyance lumen tube, which is shaped so as to define a delivery-handle fluid-conveyance lumen in fluid communication with the fluid-retaining chamber and the catheter fluid-conveyance lumen.

For some applications, the delivery handle includes a delivery-handle lumen shaft, which is disposed within the delivery-handle fluid-conveyance lumen, and which extends from the catheter lumen shaft and longitudinally slidable with respect to the delivery handle.

For some applications, the delivery handle further includes a distal user control, which is configured to release the balloon-based implant from the delivery system.

For some applications, the delivery handle includes a window opening, and an external surface of the fluid-retaining chamber is marked with a scale that is visible through the window opening, to enable a user to monitor an amount of the fluid present within the fluid-retaining chamber.

For some applications, the apparatus further includes a cannula extension, which is connected at one end of the cannula extension in fluid communication with the fluid-retaining chamber.

For some applications, the delivery handle further includes a plunger pusher, and the double-threaded tube is shaped so as to define: a first thread that is threadedly coupled to a corresponding second thread defined by the plunger pusher, and a third thread that is threadedly coupled to a corresponding fourth thread defined by the actuator.

For some applications:
the delivery handle includes a safety latch, which is configured to assume locked and unlocked states,
the safety latch, when in the locked state, blocks the double-threaded tube from completion of concurrently (a) expelling at least some of the fluid from the fluid-retaining chamber into the inflatable balloon and (b) shortening the length of the balloon-based implant, and
the safety latch, when in the unlocked state, allows further rotation of the proximal rotatable user-control knob in the first rotation direction to complete concurrently (a) expelling at least some of the fluid from the fluid-retaining chamber into the inflatable balloon and (b) shortening the length of the balloon-based implant.

For some applications, the delivery handle further includes a length-maintaining fluid user-control knob, and the delivery handle is configured such that rotation of the length-maintaining fluid user-control knob, in a first rotational direction, proximally moves the fluid-retaining chamber within the delivery handle while the plunger remains longitudinally stationary, thereby expelling additional fluid from the fluid-retaining chamber into the balloon of the balloon-based implant without changing the length of the balloon-based occlusion device.

For some applications, the delivery system further includes a delivery catheter that includes the fluid-conveyance lumen catheter and the catheter lumen shaft, and the fluid-retaining chamber is disposed within the delivery catheter, in a proximal or distal position along the delivery catheter. For some applications, the fluid-retaining chamber is shaped so as to define two sub-chambers, having a shaft opening allowing the collection of blood from the patient circulatory system into the fluid-retaining chamber, and the injection of the collected blood into the balloon-based occlusion device.

For some applications, an occlusion system is provided that includes the delivery system and further includes the balloon-based occlusion device. For some applications, the balloon-based occlusion device includes an actuating shaft, which is (a) disposed at least partially within the balloon, (b) connected to a distal end portion of the balloon, and (c) longitudinally moveable with respect to a proximal end portion of the balloon so as to set a distance between the distal and the proximal end portions of the balloon. For some applications, the balloon-based occlusion device further includes a locking mechanism, which is configured to assume locked and unlocked states, and which is configured, when in the locked state, to maintain, between the distal end portion of the balloon and the proximal end portion of the balloon, the distance set using the actuating shaft.

There is further provided, in accordance with an application of the present invention, a delivery system for delivering and deploying an implantable balloon-based occlusion device that includes an inflatable balloon, the delivery system including:
a delivery handle, which includes:
a fluid-retaining chamber, delimited by a tubular barrel having a proximal end, a distal end, and an internal surface;
a plunger, which is slidingly disposed in the fluid-retaining chamber so as to provide a movable membrane; and
a proximal rotatable user-control knob;
a fluid-conveyance lumen catheter, which is shaped so as to define a catheter fluid-conveyance lumen in fluid communication (a) with the fluid-retaining chamber and (b) with the inflatable balloon of the balloon-based occlusion device when the fluid-conveyance lumen catheter is coupled to the inflatable balloon; and
a catheter lumen shaft, which is in reversible connection with the balloon-based occlusion device, longitudinally slidable with respect to the delivery handle,
wherein the delivery handle is configured such that rotation of the proximal rotatable user-control knob in a first rotational direction concurrently (a) expels at least some of the fluid from the fluid-retaining chamber into the inflatable balloon of the balloon-based occlusion device, via the catheter fluid-conveyance lumen, and (b) shortens a length of the balloon-based occlusion device by proximally pulling the catheter lumen shaft.

For some applications, the delivery handle is configured such that rotation of the proximal rotatable user-control knob in a second rotational direction opposite the first rotational direction concurrently (a) withdraws at least some of the fluid into the fluid-retaining chamber from the inflatable balloon of the balloon-based occlusion device, via the catheter fluid-conveyance lumen, and (b) elongates the length of the balloon-based occlusion device by distally pushing the catheter lumen shaft.

For some applications, the catheter lumen shaft is disposed within the catheter fluid-conveyance lumen.

For some applications, the fluid-retaining chamber is disposed within the delivery handle.

For some applications, the delivery handle further includes a distal user control, which is configured to release the balloon-based implant from the delivery system.

For some applications, the delivery handle includes a window opening, and an external surface of the fluid-retaining chamber is marked with a scale that is visible through the window opening, to enable a user to monitor an amount of the fluid present within the fluid-retaining chamber.

For some applications, the delivery handle includes a delivery-handle fluid-conveyance lumen tube, which is shaped so as to define a delivery-handle fluid-conveyance lumen in fluid communication with the fluid-retaining chamber and the catheter fluid-conveyance lumen.

For some applications, the delivery handle includes a delivery-handle lumen shaft, which is disposed within the delivery-handle fluid-conveyance lumen, and which extends from the catheter lumen shaft and longitudinally slidable with respect to the delivery handle.

For some applications, the apparatus further includes a cannula extension, which is connected at one end of the cannula extension in fluid communication with the fluid-retaining chamber.

For some applications, the delivery handle further includes a length-maintaining fluid user-control knob, and the delivery handle is configured such that rotation of the length-maintaining fluid user-control knob, in a first rotational direction, proximally moves the fluid-retaining chamber within the delivery handle while the plunger remains longitudinally stationary, thereby expelling additional fluid from the fluid-retaining chamber into the balloon of the balloon-based implant without changing the length of the balloon-based occlusion device.

For some applications, the delivery handle further includes a double-threaded tube, which is connected to the proximal rotatable user-control knob, and which connects and couples actuation of the plunger into the fluid-retaining chamber and longitudinal sliding of the catheter lumen shaft.

For some applications:

the delivery handle further includes an actuator, connected to the catheter lumen shaft, and the delivery handle is configured such that rotation of the proximal rotatable user-control knob in the first rotational direction activates the double-threaded tube to concurrently (a) expel at least some of the fluid from the fluid-retaining chamber into the inflatable balloon of the balloon-based occlusion device, via the catheter fluid-conveyance lumen, and (b) shorten the length of the balloon-based occlusion device by proximally moving the actuator, which in turn proximally pulls the catheter lumen shaft For some applications, the delivery handle is configured such that rotation of the proximal rotatable user-control knob in a second rotational direction opposite the first rotational direction, activates the double-threaded tube to concurrently (a) withdraw at least some of the fluid into the fluid-retaining chamber from the inflatable balloon of the balloon-based occlusion device, via the catheter fluid-conveyance lumen, and (b) elongate the length of the balloon-based occlusion device by distally moving the actuator, which in turn distally pushes the catheter lumen shaft.

For some applications, the delivery handle further includes a plunger pusher and an actuator connected to the catheter lumen shaft, and the double-threaded tube is shaped so as to define: a first thread that is threadedly coupled to a corresponding second thread defined by the plunger pusher, and a third thread that is threadedly coupled to a corresponding fourth thread defined by the actuator.

For some applications:

the delivery handle includes a safety latch, which is configured to assume locked and unlocked states, the safety latch, when in the locked state, blocks the double-threaded tube from completion of concurrently (a) expelling at least some of the fluid from the fluid-retaining chamber into the inflatable balloon and (b) shortening the length of the balloon-based implant, and the safety latch, when in the unlocked state, allows further rotation of the proximal rotatable user-control knob in the first rotation direction to complete concurrently (a) expelling at least some of the fluid from the fluid-retaining chamber into the inflatable balloon and (b) shortening the length of the balloon-based implant.

For some applications, an occlusion system is provided that includes the delivery system and further includes the balloon-based occlusion device. For some applications, the balloon-based occlusion device includes an actuating shaft, which is (a) disposed at least partially within the balloon, (b) connected to a distal end portion of the balloon, and (c) longitudinally moveable with respect to a proximal end portion of the balloon so as to set a distance between the distal and the proximal end portions of the balloon. For some applications, the balloon-based occlusion device further includes a locking mechanism, which is configured to assume locked and unlocked states, and which is configured, when in the locked state, to maintain, between the distal end portion of the balloon and the proximal end portion of the balloon, the distance set using the actuating shaft.

There is still further provided, in accordance with an application of the present invention, a method for delivering and deploying an implantable balloon-based occlusion device that includes an inflatable balloon, the method including, using a delivery system:

filling, with fluid, a fluid-retaining chamber of the delivery system, the fluid-retaining chamber delimited by a tubular barrel having a proximal end, a distal end, and an internal surface, wherein a plunger is slidingly disposed in the fluid-retaining chamber so as to provide a movable membrane;

using a delivery catheter of the delivery system, advancing the implantable balloon-based occlusion device to a desired site in a body of a subject, the delivery catheter including (i) a fluid-conveyance lumen catheter, which is shaped so as to define a catheter fluid-conveyance lumen in fluid communication (a) with the fluid-retaining chamber and (b) with the inflatable balloon of the balloon-based occlusion device when the fluid-conveyance lumen catheter is coupled to the inflatable balloon, and (ii) a catheter lumen shaft, which is in reversible connection with the balloon-based occlusion device, longitudinally slidable with respect to the delivery handle; and thereafter, rotating a proximal rotatable user-control knob of a delivery handle of the delivery system in a first rotation direction, such that that the delivery system concurrently (a) expels at least some of the fluid from the fluid-retaining chamber into the inflatable balloon of the balloon-based occlusion device, via the catheter fluid-conveyance lumen, and (b) shortens a length of the balloon-based occlusion device by proximally pulling the catheter lumen shaft.

For some applications, the method further includes, after rotating the proximal rotatable user-control knob in the first rotation direction, rotating the proximal rotatable user-control knob in a second rotational direction opposite the first rotational direction, such that the delivery system concurrently (a) withdraws at least some of the fluid into the fluid-retaining chamber from the inflatable balloon of the balloon-based occlusion device, via the catheter fluid-conveyance lumen, and (b) elongates the length of the balloon-based occlusion device by distally pushing the catheter lumen shaft.

For some applications, rotating the proximal rotatable user-control knob in the first rotation direction rotates a double-threaded tube of the delivery handle.

For some applications:

the delivery handle includes a safety latch, which is configured to assume locked and unlocked states, and rotating the proximal rotatable user-control knob in the first rotation direction includes, while the safety latch is in the locked state, rotating the proximal rotatable user-control knob in the first rotation direction until the safety latch blocks the delivery system from completion of concurrently (a) expelling at least some of the fluid from the fluid-retaining chamber into the inflatable balloon and (b) shortening the length of the balloon-based implant.

For some applications, the method further includes, after rotating the proximal rotatable user-control knob in the first rotation direction until the safety latch blocks the delivery system from the completion:

assessing whether the balloon-based occlusion device is properly deployed; and upon assessing that balloon-based occlusion device is properly deployed, transitioning the safety latch to the unlocked state, and further rotating the proximal rotatable user-control knob in the first rotation direction to complete concurrently (a) expelling at least some of the fluid from the fluid-retaining chamber into the inflatable balloon and (b) shortening the length of the balloon-based implant.

For some applications, the method further includes, after rotating the proximal rotatable user-control knob in the first rotation direction until the safety latch blocks the delivery system from the completion:

assessing whether the balloon-based occlusion device is properly deployed; and upon assessing that balloon-based occlusion device has a desired length and the balloon of the balloon-based occlusion device does not contain a desired amount fluid, adjusting an amount of the fluid in the balloon of the balloon-based occlusion device by rotating a length-maintaining fluid user-control knob of the delivery handle to move the fluid-retaining chamber within the delivery handle while the plunger remains longitudinally stationary, thereby adjusting the amount of the fluid in the balloon of the balloon-based implant without changing the length of the balloon-based occlusion device.

For some applications, the method further includes using a distal user control of the delivery handle to release the balloon-based implant from the delivery system.

For some applications, filling the fluid-retaining chamber includes filling the fluid-retaining chamber from a fluid source external to the delivery system, via a cannula extension, which is connected at one end of the cannula extension in fluid communication with the fluid-retaining chamber.

The present invention will be more fully understood from the following detailed description of embodiments thereof, taken together with the drawings, in which:

BRIEF DESCRIPTION OF THE DRAWINGS

FIGS. 5A-F are schematic illustrations of a delivery catheter, in accordance with an application of the present invention;

DETAILED DESCRIPTION OF APPLICATIONS

Figure 1:
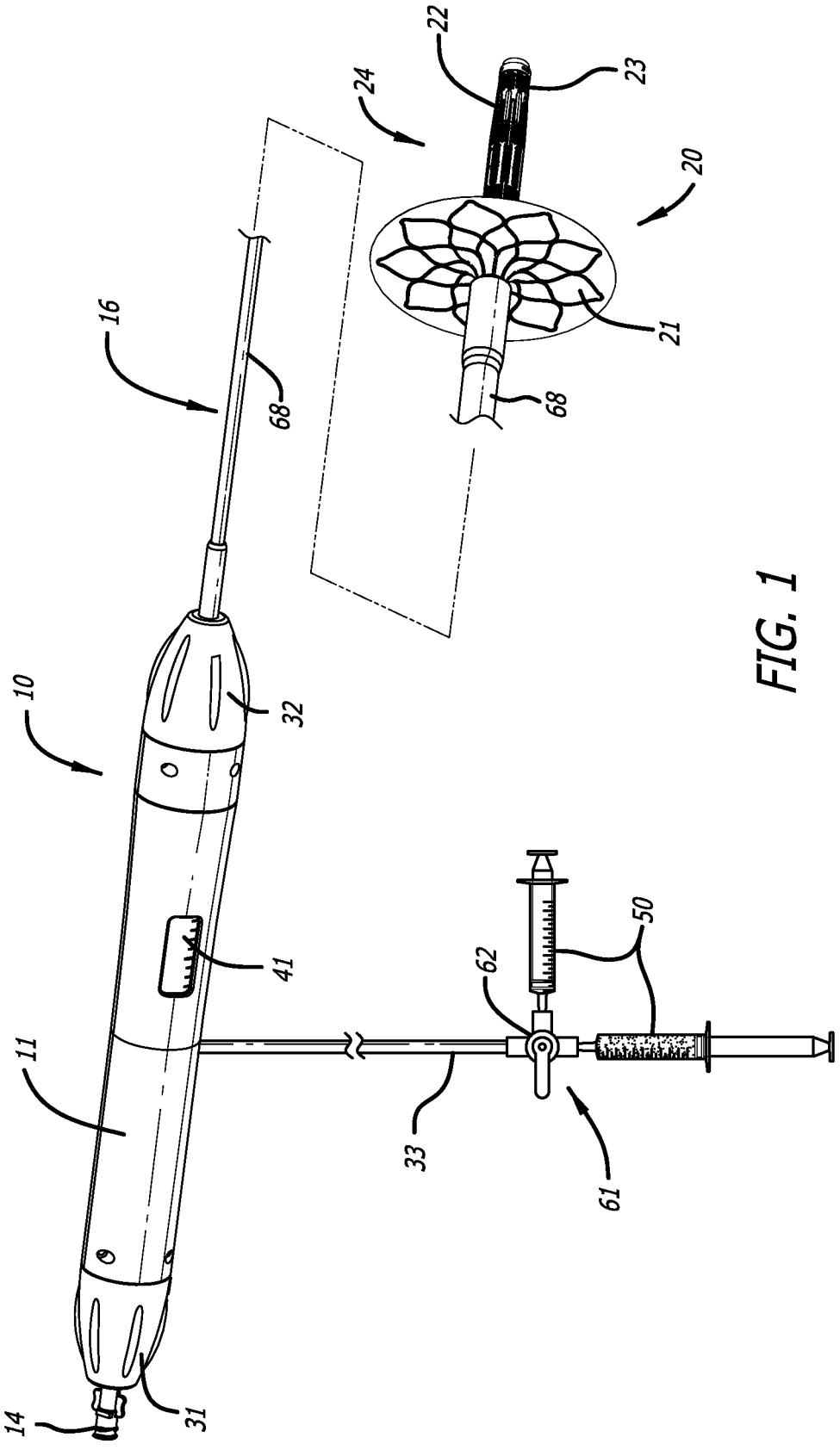
FIG. 1 is a schematic illustration of a delivery system connected to an implantable balloon-based implant that is in a noninflated and non-deployed configuration, in accordance with an application of the present invention.

FIG. 1 is a schematic illustration of a delivery system 10 connected to an implantable balloon-based implant 20 that is in a noninflated and non-deployed configuration 24, in accordance with an application of the present invention. Implantable balloon-based implant 20 includes an inflatable balloon 22. Implantable balloon-based implant 20 is not an element of delivery system 10. Delivery system 10 and the other delivery systems described herein are typically transcatheter delivery systems that enable percutaneous deployment of balloon-based implant 20.

Reference is also made to FIGS. 2A-H, which are schematic illustrations of a method of using delivery system 10 for delivering and deploying balloon-based implant 20, in accordance with an application of the present invention. FIGS. 2A-D show implantable balloon-based implant 20 in noninflated and non-deployed configuration 24, and FIGS. 2E-H show implantable balloon-based implant 20 in a fully-inflated and shortened deployed configuration 25.

For some applications, balloon-based implant 20 is a balloon-based occlusion device. For example, the balloon-based occlusion device may comprise a proximal LAA-orifice cover 21 and inflatable balloon 22, surrounded by a conformable balloon frame 23. Optionally, the balloon-based occlusion device be configured as described hereinabove with reference to FIGS. 6-10 and/or may implement any of the techniques described in the patent applications incorporated hereinbelow by reference.

Delivery system 10 comprises a delivery handle 11 and a delivery catheter 16. Delivery handle 11 comprises a proximal rotatable user-control knob 31 that is configured to activate a double-threaded tube 46 within handle 11, as described hereinbelow with reference to FIGS. 2B-D and 2F-G. Optionally, delivery handle 11 further comprises a distal user control 32 that is configured to release balloon-based implant 20 from delivery system 10 (typically from delivery catheter 16), such as described hereinbelow with reference to FIG. 2H.

Delivery handle 11 further comprises a fluid-retaining chamber 41, which is delimited by a tubular barrel 34 having a proximal end 36, a distal end 38, and an internal surface 40. Delivery handle 11 further comprises a plunger 30 that is slidingly disposed in fluid-retaining chamber 41 so as to define a distal movable membrane 45 (i.e., a distal surface of the head of plunger 30) to draw fluid into fluid-retaining chamber 41 and expel fluid out of fluid-retaining chamber 41, thereby filling and unfilling fluid-retaining chamber 41, respectively. For example, the fluid may comprise saline. Optionally the fluid may comprise a contrast agent.

Optionally, an external surface of fluid-retaining chamber 41 is marked with a scale that is visible through a window opening on delivery handle 11, to enable a user to monitor the amount of fluid present within fluid-retaining chamber 41 within delivery handle 11.

Figures 2A, 2B:
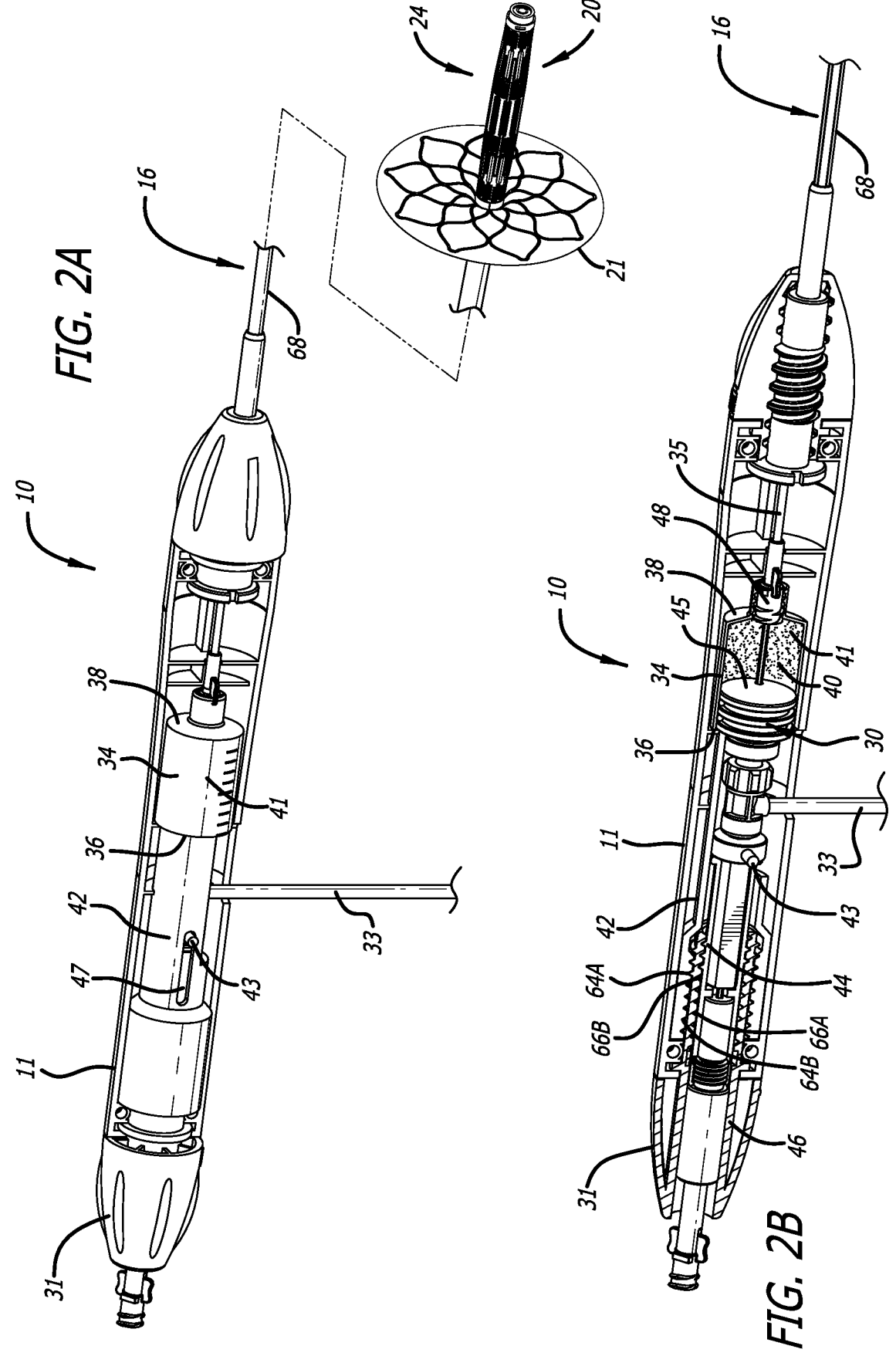
FIGS. 2A-H are schematic illustrations of a method of using the delivery system of FIG. 1 for delivering and deploying the balloon-based implant, in accordance with an application of the present invention.
Figure 2C:
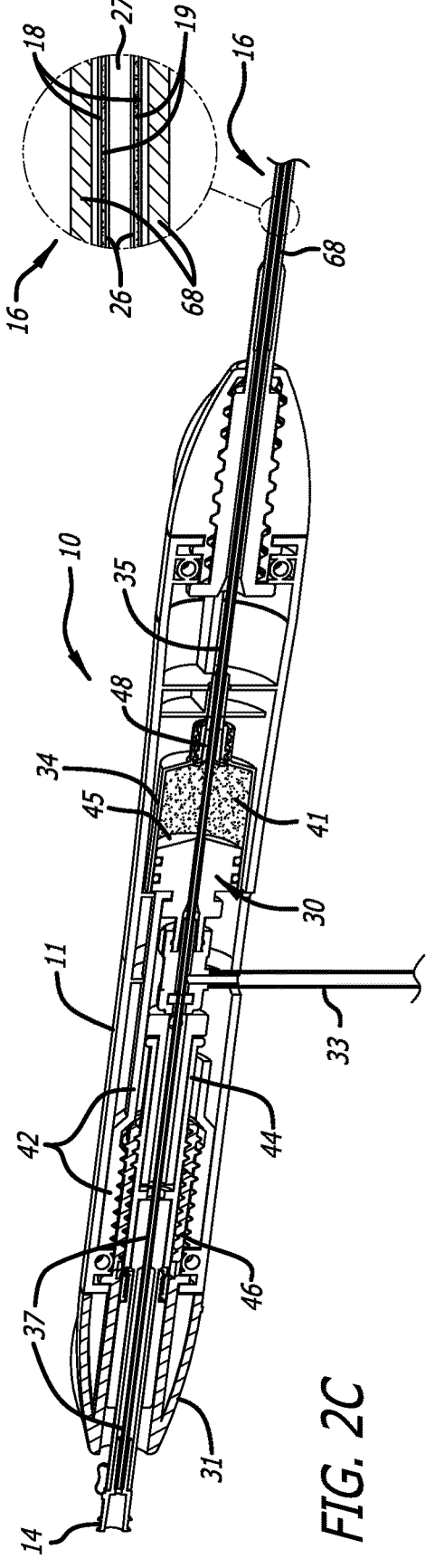

As shown in FIG. 2C, delivery catheter 16 comprises:

a fluid-conveyance lumen catheter 18, which is shaped so as to define a catheter fluid-conveyance lumen 19 in fluid communication (a) with fluid-retaining chamber 41 (as described below) and (b) with inflatable balloon 22 of balloon-based implant 20 when fluid-conveyance lumen catheter 18 is coupled to inflatable balloon 22; a single integral shaft may define both fluid-conveyance lumen catheter 18 and delivery-handle fluid-conveyance lumen tube 35, or two discrete shafts may define fluid-conveyance lumen catheter 18 and delivery-handle fluid-conveyance lumen tube 35, respectively, and be coupled together; and a catheter lumen shaft 26, which is disposed within catheter fluid-conveyance lumen 19, and which is in direct reversible connection with balloon-based implant 20 (for example, as described hereinbelow with reference to FIGS. 6-9C), longitudinally slidable with respect to delivery handle 11 to shorten or lengthen a length of balloon-based implant 20.

It is noted that because catheter lumen shaft 26 is typically disposed within catheter fluid-conveyance lumen 19, only a portion of the volume of catheter fluid-conveyance lumen 19 is available for passage of the fluid, i.e., the space between an inner surface of fluid-conveyance lumen catheter 18 and an outer surface of catheter lumen shaft 26.

Figure 2D:
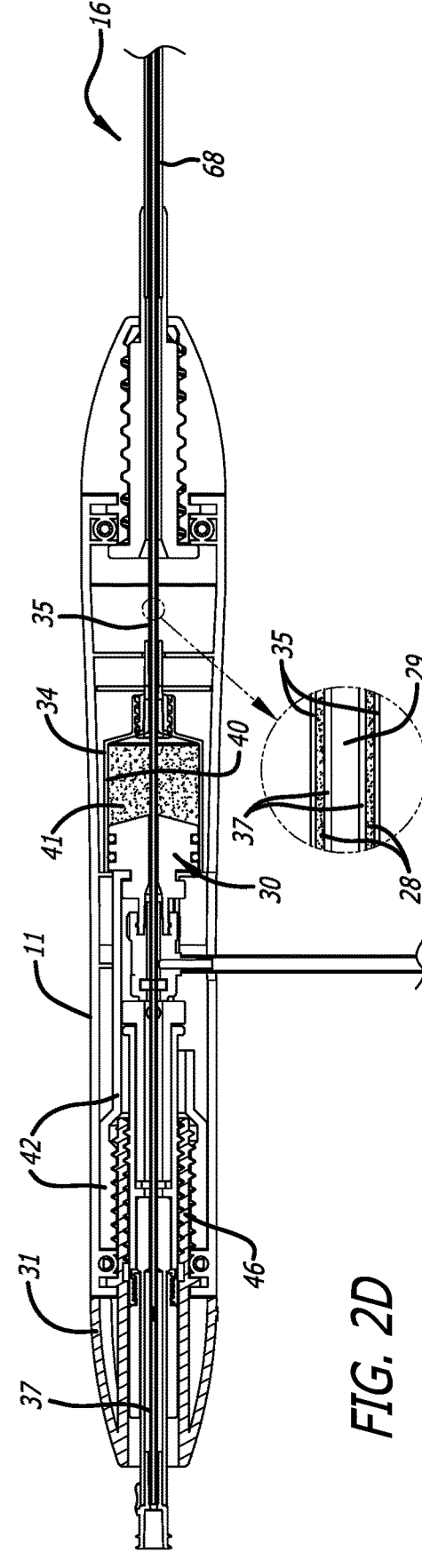

As shown in FIG. 2D, delivery handle 11 comprises:

a delivery-handle fluid-conveyance lumen tube 35, which is shaped so as to define a delivery-handle fluid-conveyance lumen 28 in fluid communication with (a) a port 48 at a distal end of fluid-retaining chamber 41 (labeled in FIGS. 2B and 2C) and (b) catheter fluid-conveyance lumen 19, for expelling fluid out of fluid-retaining chamber 41, into catheter fluid-conveyance lumen 19, and to inflatable balloon 22 of balloon-based implant 20. The expulsion of the fluid from fluid-retaining chamber 41 inflates inflatable balloon 22 of balloon-based implant 20 during deployment of the implant; and a delivery-handle lumen shaft 37, which is disposed within delivery-handle fluid-conveyance lumen 28, and which is extends from catheter lumen shaft 26 and longitudinally slidable with respect to delivery handle 11; a single integral shaft may define both delivery-handle lumen shaft 37 and catheter lumen shaft 26, or two discrete shafts may define delivery-handle lumen shaft 37 and catheter lumen shaft 26, respectively, and be coupled together.

It is noted that because delivery-handle lumen shaft 37 is typically disposed within delivery-handle fluid-conveyance lumen 28, only a portion of the volume of delivery-handle fluid-conveyance lumen 28 is available for passage of the fluid, i.e., the space between an inner surface of delivery-handle fluid-conveyance lumen tube 35 and an outer surface of delivery-handle lumen shaft 37.

Typically, a proximal end of delivery-handle fluid-conveyance lumen tube 35 is coupled to port 48.

Delivery system 10 further comprises a cannula extension 33, which is connected at one end of the cannula extension in fluid communication with fluid-retaining chamber 41. The other end of cannula extension 33 is configured to be coupled in fluid connection with a fluid source, such as one or more conventional syringes 50. To this end, cannula extension 33 typically comprises a connector 61, such as a valve 62 (e.g., a 3-way valve) or a stopcock, which optionally comprises a valve. Cannula extension 33 may be used to fill fluid-retaining chamber 41 at the beginning of the implantation procedure, such as by creating a vacuum within fluid-retaining chamber 41 using a first one of syringes 50, changing a position of 3-way valve 62, and then injecting fluid into fluid-retaining chamber 41 using a second one of syringes 50. Optionally, cannula extension 33 may be used during or after the distal advancement of plunger 30 into fluid-retaining chamber 41, in order to insert additional fluid into fluid-retaining chamber 41 and consequently into balloon 22 of balloon-based implant 20.

For some applications, catheter lumen shaft 26 is shaped so as to define a catheter guidewire lumen 27 (labeled in FIG. 2C), through which a guidewire and/or a fluid, such as a contrast agent, may be passed. For these applications, delivery handle 11 typically further comprises a delivery-handle guidewire lumen 29 (labeled in FIG. 2D) having a proximal lumen entrance 14 and a distal end in communication with catheter guidewire lumen 27. While balloon-based implant 20 is in the noninflated and non-deployed configuration 24, a guidewire (not shown) may be passed through lumen entrance 14 of delivery-handle fluid-conveyance lumen 28, delivery-handle guidewire lumen 29, and a guidewire lumen defined by balloon-based implant 20, for guiding the balloon-based implant and delivery catheter 16 of delivery system 10 to the target area in the subject's body. The guidewire may be withdrawn proximally after the balloon-based implant reaches the target site.

For some applications, as show in FIG. 2A, delivery handle 11 comprises a plunger pusher 42. Optionally, delivery handle 11 further comprises a longitudinal-action position pin 43, which protrudes from a longitudinal opening 47 through plunger pusher 42 and is positioned distally within longitudinal opening 47. The length of longitudinal opening 47 sets a maximum distance that pin 43 can move, thereby limiting the maximum distance plunger pusher 42 can move, and setting a maximum amount of fluid that can be expelled from fluid-retaining chamber 41. Because pin 43 is rotationally constrained by longitudinal opening 47, the pin may also help stabilize the movement of plunger pusher 42, by inhibiting rotation of plunger pusher 42 when it moves longitudinally.

As shown in FIGS. 2B-D and 2F-G, double-threaded tube 46 is connected to proximal rotatable user-control knob 31. Double-threaded tube 46 is shaped so as to define:

a first thread 64A that is threadedly coupled to a corresponding second thread 64B defined by plunger pusher 42 (for example, first thread 64A may be an external thread, and second thread 64B may be an internal thread, such as shown, or vice versa, as described hereinbelow regarding balloon-based implant 120 with reference to FIGS. 4A-F), and a third thread 66A that is threadedly coupled to a corresponding fourth thread 66B defined by an actuator 44, which is described hereinbelow (for example, third thread 66A may be an internal thread, and fourth thread 66B may be an external thread, such as shown, or vice versa (configuration not shown)).

Actuator 44 is disposed longitudinally slidable in delivery handle 11, coupled to delivery-handle lumen shaft 37, which, as mentioned above, extends from catheter lumen shaft 26. Actuator 44 is longitudinally movable with respect to delivery handle 11 so to shorten or elongate balloon-based implant 20.

Delivery handle 11 is configured such that the rotation of proximal rotatable user-control knob 31 actuates plunger pusher 42 and actuator 44 by rotating double-threaded tube 46, such that rotation of proximal rotatable user-control knob 31:

in a first rotational direction, such as shown in the transition between FIGS. 2B-D and FIGS. 2F-G, activates double-threaded tube 46 to concurrently (a) expel at least some of the fluid from fluid-retaining chamber 41 into inflatable balloon 22 of balloon-based implant 20, via catheter fluid-conveyance lumen 19, by distally moving plunger pusher 42, which in turn distally advances plunger 30 within fluid-retaining chamber 41; and (b) shorten a length of balloon-based implant 20 (optionally, including a frame 23 thereof), by proximally moving actuator 44, which in turn proximally pulls catheter lumen shaft 26 via delivery-handle lumen shaft 37, and in a second rotational direction opposite the first rotational direction, activates double-threaded tube 46 to concurrently (a) withdraw at least some of the fluid into fluid-retaining chamber 41 from inflatable balloon 22 of balloon-based implant 20, via catheter fluid-conveyance lumen 19, and (b) elongate the length of balloon-based implant 20 (optionally, including a frame 23 thereof), by distally moving actuator 44, which in turn distally pushes catheter lumen shaft 26 via delivery-handle lumen shaft 37 (configuration not shown, but equivalent to transitioning back from FIGS. 2F-G to FIGS. 2B-D).

The result of the first transition described above (caused by rotation of proximal rotatable user-control knob 31 in the first rotational direction) is to cause the distal sliding of distal movable membrane 45 of plunger 30 within fluid-retaining chamber 41 and the fluid inflation of balloon 22 of balloon-based implant 20, concurrently with the shortening of balloon-based implant 20 (e.g., balloon frame 23 thereof), which is connected to actuator 44 via catheter lumen shaft 26 and delivery-handle lumen shaft 37, to bring balloon-based implant 20 to fully-inflated and shortened deployed configuration 25, as shown in FIGS. 2E-H.

The second transition described above (caused by rotation of proximal rotatable user-control knob 31 in the second rotational direction) is the opposite, namely concurrent (a) refilling of fluid-retaining chamber 41 with fluid from balloon 22 and (b) lengthening of balloon-based implant 20. This may be desired in order to reposition or remove the implant before completion of the implantation procedure, and/or in order to adjust the implant size to better match a cardiovascular defect.

Delivery handle 11 is configured such that the rotation of proximal rotatable user-control knob 31 moves plunger 30 within fluid-retaining chamber 41 in a first longitudinal direction by a first distance, and moves catheter lumen shaft 26 in a second longitudinal direction, opposite the first longitudinal direction, by a second distance. For some applications, a ratio of the first and the second distances remains constant over all possible degrees of the rotation proximal rotatable user-control knob 31. As a result, a ratio of (a) the volume of fluid transferred out of or into fluid-retaining chamber 41 and (b) a change in the length of the balloon-based implant 20 remains constant over all possible degrees of the rotation proximal rotatable user-control knob 31. This is typically the case during rotation of the proximal rotatable user-control knob 31 in both the first and the second rotational directions.

Figures 2E, 2F:
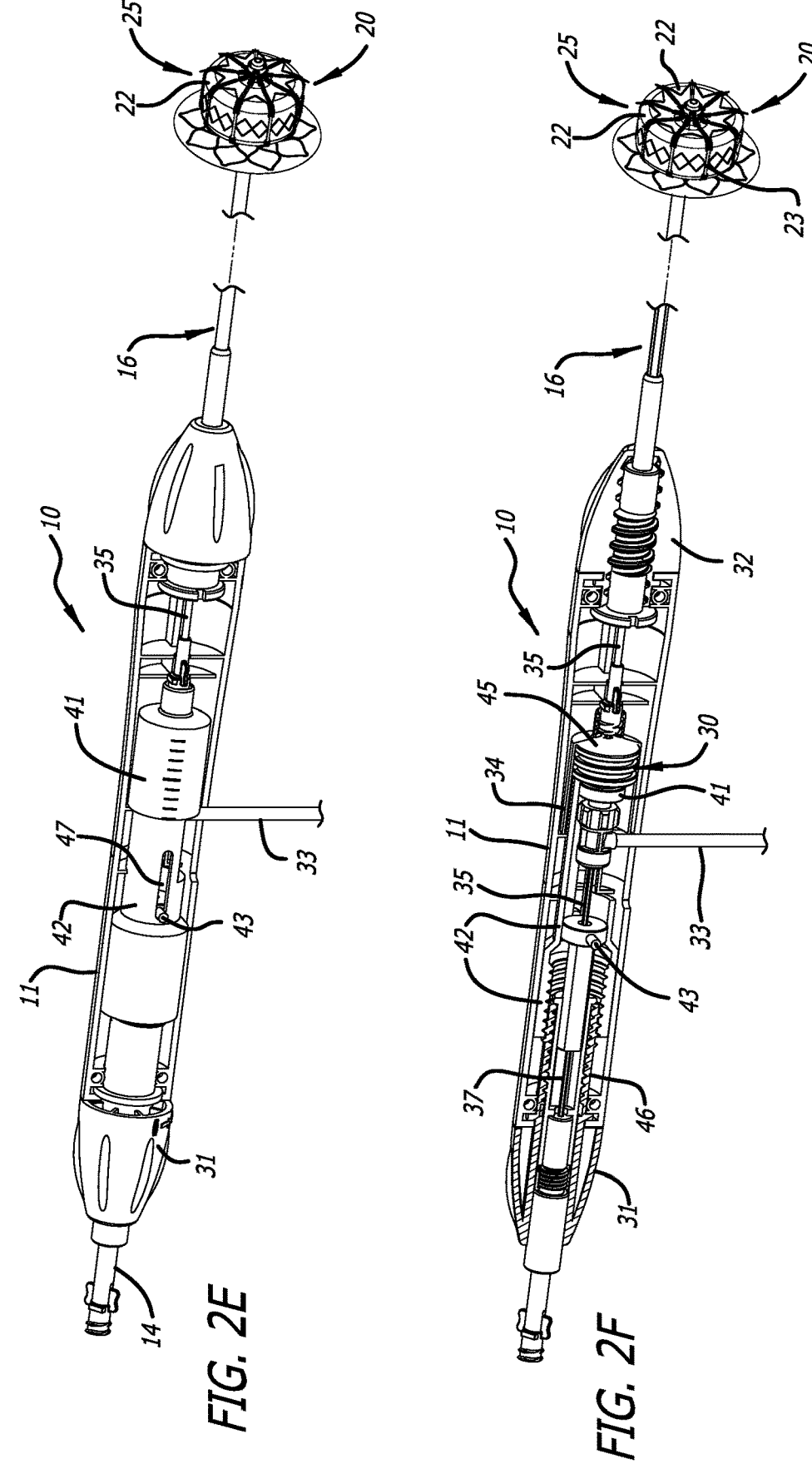

FIG. 2E is a cross-sectional view of delivery system 10 highlighting the longitudinal-action position pin 43, which extends radially outward from longitudinal opening 47 on plunger pusher 42 and is positioned proximally within the longitudinal opening, as result of the shortening of balloon-based implant 20 to deployed configuration 25 actuated by rotation of proximal rotatable user-control knob 31. The movement of actuator 44 and the related shortening of balloon-based implant 20 is indicated by the position of pin 43, which is visible through plunger pusher 42.

In this phase, a contrast medium fluid may be injected (such as from a syringe) into lumen entrance 14, through delivery-handle guidewire lumen 29 and catheter guidewire lumen 27, to exit distally to balloon-based implant 20, to visually evaluate by x-ray imaging the adherence of the balloon-based implant to the surrounding target anatomy.

Figures 2G, 2H:
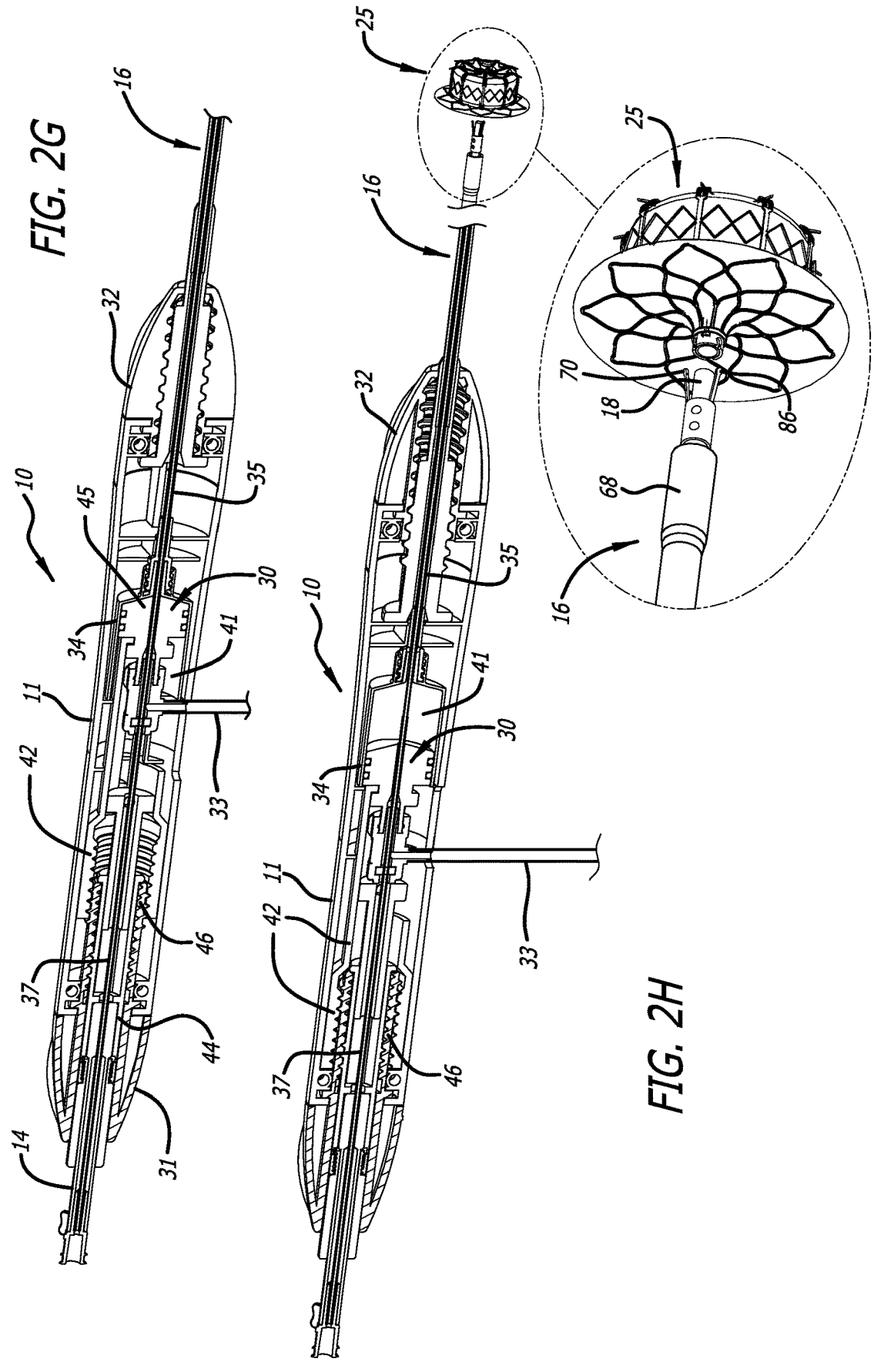

FIGS. 2E-G show delivery system 10 after it has been actuated to transition balloon-based implant 20 to its fully-inflated and shortened deployed configuration 25. If it is desired to introduce additional fluid into balloon 22, such as to achieve greater adherence of balloon-based implant 20 with the surround anatomy, additional fluid may be introduced from cannula extension 33 into delivery-handle fluid-conveyance lumen 28 via fluid-retaining chamber 41 and to balloon 22 of balloon-based implant 20.

The distal end of catheter lumen shaft 26 is decoupled from balloon-based implant 20, such as by rotation of catheter lumen shaft 26, e.g., by rotation of proximal lumen entrance 14. For example, the decoupling techniques described hereinbelow with reference to FIGS. 7A-B may be used.

Reference is made to FIG. 2H. For some applications, delivery catheter 16 further comprises an outer implant-coupling tube 68, which is configured to hold delivery catheter 16 coupled to balloon-based implant 20. For example, a distal connector 86 of delivery catheter 16 may comprise one or more legs that engage one or more respective coupling sites (e.g., slots) of a proximal connector of balloon-based implant 20, such as labeled in FIG. 2H. For example, the legs may be configured to biased radially outward when in an unconstrained, resting state, and may be held radially inward engaging the coupling sites of the proximal connector by outer implant-coupling tube 68, as shown in FIG. 1. Proximal withdrawal of outer implant-coupling tube 68 with respect to balloon-based implant 20 releases the legs, as shown in FIG. 2H (and FIG. 9B, described hereinbelow).

For some applications, activation of distal user control 32 disconnects balloon-based implant 20 from delivery catheter 16 and thus from delivery system 10. For example, distal user control 32 may comprise a rotatable knob, rotation of which disconnects balloon-based implant 20 from delivery catheter 16, in which case distal user control 32 may have a threaded connection with a tube of delivery handle 11, such that the rotation proximally moves outer implant-coupling tube 68 with respect to delivery handle 11. Alternatively, distal user control 32 may be slidable with respect to delivery handle 11, such that sliding of the user control in a proximal direction proximally moves outer implant-coupling tube 68 with respect to delivery handle 11.

For some applications, fluid-retaining chamber 41 has a maximum volume of 50 ml, e.g., 20 ml.

For some applications, plunger 30 has a length of between 5 mm and 25 mm, typically 10 mm, and distal movable membrane 45 has a diameter of between 5 mm and 30 mm, typically 15 mm.

For some applications, double-threaded tube 46 has a length of between 20 mm and 150 mm, typically 100 mm, when in a closed configuration, and/or a length of between 40 mm and 200 mm, typically 150 mm, when in an open configuration.

For some applications, double-threaded tube 46 has a diameter of between 5 and 40 mm, typically 15 mm.

For some applications:

first and second threads 64A and 64B have a number of turns of between 2 and 25 and/or a pitch of between 0.5 and 5 mm, and/or third and fourth threads 66A and 66B have a number of turns of between 2 and 25 and/or a pitch of between 0.5 and 5 mm.

Figure 3:
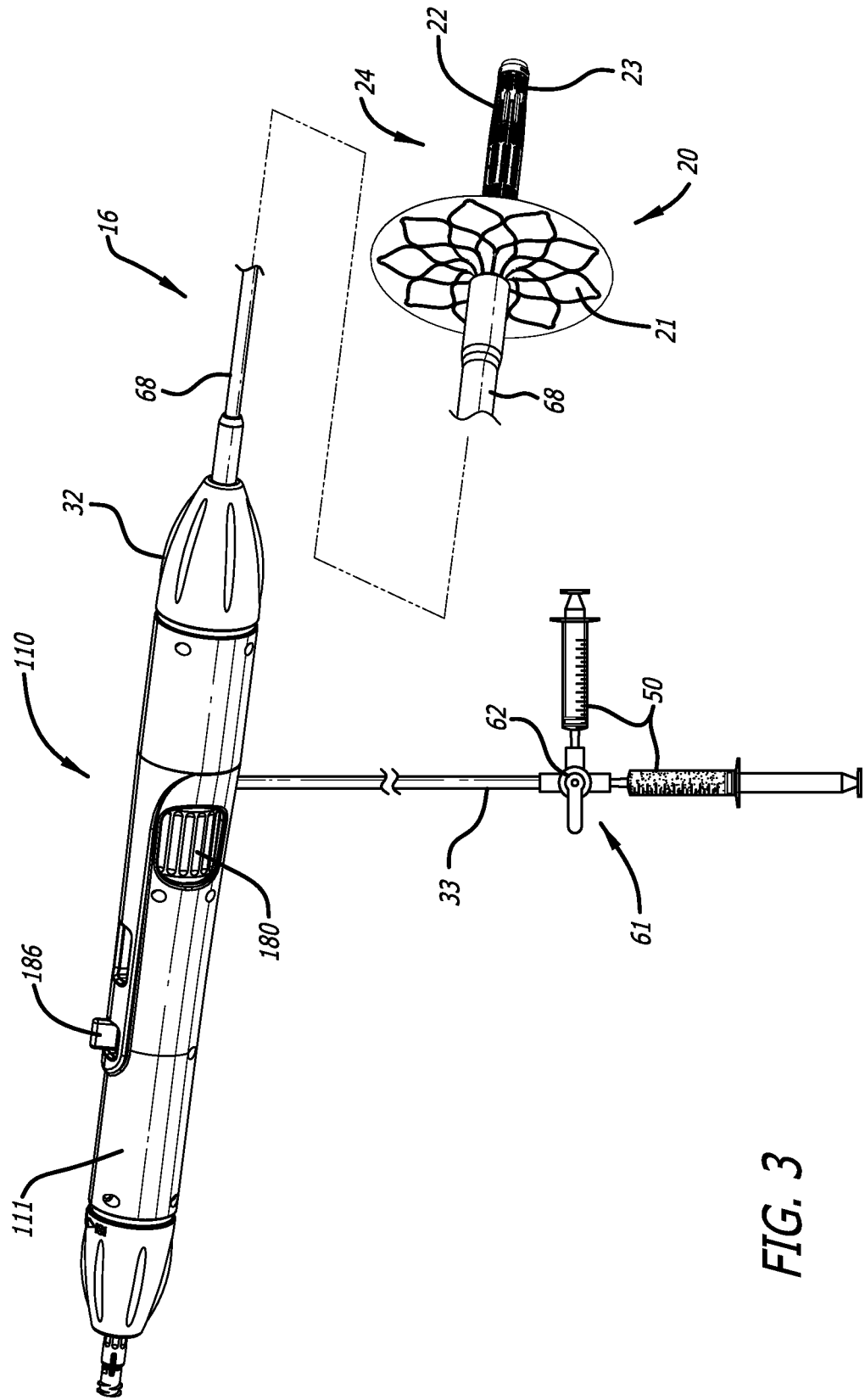
FIG. 3 is a schematic illustration of another delivery system connected to an implantable balloon-based implant that is in a noninflated and non-deployed configuration, in accordance with an application of the present invention.

Reference is now made to FIG. 3 is a schematic illustration of a delivery system 110 connected to implantable balloon-based implant 20 that is in noninflated and non-deployed configuration 24, in accordance with an application of the present invention. Other than as described hereinbelow, delivery system 110 is similar to delivery system 10, described hereinabove with reference to FIGS. 1 and 2A-H, and like numerals refer to like parts. Optionally, delivery system 110 may implement any of the features of delivery system 10, mutatis mutandis.

Reference is also made to FIGS. 4A-F, which are schematic illustrations of a method of using delivery system 110 for delivering and deploying balloon-based implant 20, in accordance with an application of the present invention.

Delivery system 110 comprises a delivery handle 111 and delivery catheter 16. Delivery handle 111 comprises proximal rotatable user-control knob 31 that is configured to activate a double-threaded tube 146 within handle 111. Optionally, delivery handle 111 further comprises distal user control 32 that is configured to release balloon-based implant 20 from delivery catheter 16, such as described hereinabove for delivery system 10 with reference to FIG. 2H.

Delivery handle 111 further comprises a fluid-retaining chamber 141. Delivery handle 111 further comprises plunger 30 that is slidingly disposed in fluid-retaining chamber 141 so as to define distal movable membrane 45 (i.e., a distal surface of the head of plunger 30) to draw fluid into fluid-retaining chamber 141 and expel fluid out of fluid-retaining chamber 141, thereby filling and unfilling fluid-retaining chamber 141, respectively. As described below, plunger 30 and fluid-retaining chamber 141 may longitudinally move with each other either by longitudinal movement of plunger 30 or by longitudinal movement of fluid-retaining chamber 141. For example, the fluid may comprise saline. Optionally the fluid may comprise a contrast medium.

Figure 4A:
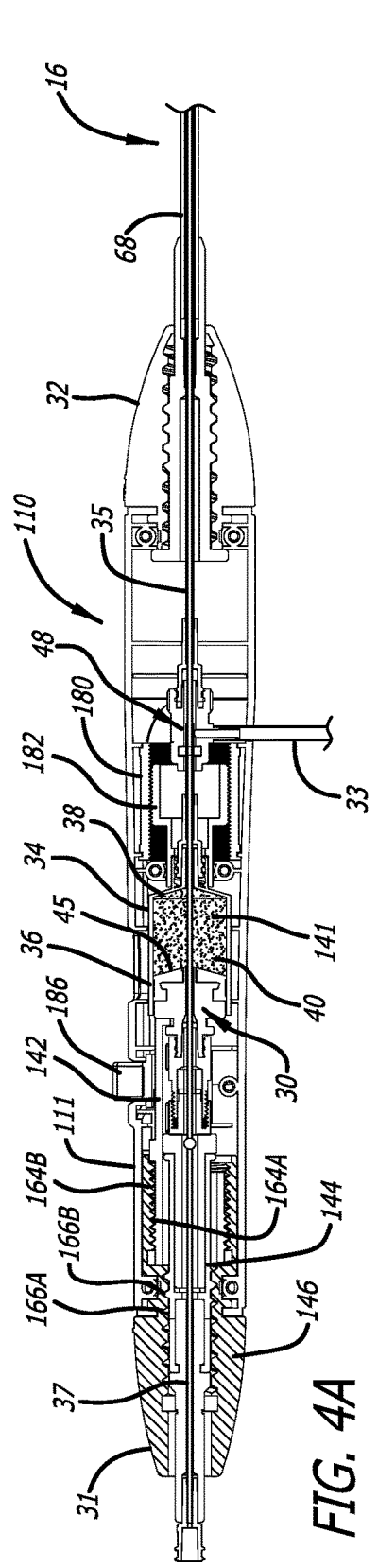
FIGS. 4A-F are schematic illustrations of a method of using the delivery system of FIG. 3 for delivering and deploying the balloon-based implant, in accordance with an application of the present invention.

For some applications, as show in FIG. 4A, delivery handle 111 comprises a plunger pusher 142. Double-threaded tube 146 is connected to proximal rotatable user-control knob 31. Double-threaded tube 146 is shaped so as to define:

a first thread 164A that is threadedly coupled to a corresponding second thread 164B defined by plunger pusher 42 (for example, first thread 164A may be an internal thread, and second thread 164B may be an external thread, such as shown, or vice versa, as described hereinabove regarding balloon-based implant 20 with reference to FIGS. 2B-D and 2F-G), and a third thread 166A that is threadedly coupled to a corresponding fourth thread 166B defined by an actuator 144, which is described hereinbelow (for example, third thread 166A may be an internal thread, and fourth thread 166B may be an external thread, such as shown, or vice versa (configuration not shown)).

For configurations in which first and third threads 164A and 166A are both internal threads (as shown) or are both external threads (configuration not shown), typically first and third threads 164A and 166A have opposite directions of threading (i.e., one is right-handed and the other left-handed). First and third threads 164A and 166A may have the same pitch as each other, or different pitches from one another.

Actuator 144 is disposed longitudinally slidable in delivery handle 111, coupled to delivery-handle lumen shaft 37, which, as mentioned above, extends from catheter lumen shaft 26. Actuator 144 is longitudinally movable with respect to delivery handle 111 so to shorten or elongate balloon-based implant 20.

The rotation of proximal rotatable user-control knob 31 actuates plunger pusher 142 and actuator 144 by rotating double-threaded tube 146, such that rotation of proximal rotatable user-control knob 31:

in a first rotational direction, such as shown in the transition between FIG. 4A and FIG. 2B, activates double-threaded tube 146 to concurrently (a) expel at least some of the fluid from fluid-retaining chamber 141 into inflatable balloon 22 of balloon-based implant 20, via catheter fluid-conveyance lumen 19, by distally moving plunger pusher 142, which in turn distally advances plunger 30 within fluid-retaining chamber 141; and (b) shorten a length of balloon-based implant 20 (optionally, including a frame 23 thereof), by proximally moving actuator 144, which in turn proximally pulls catheter lumen shaft 26 via delivery-handle lumen shaft 37, and in a second rotational direction opposite the first rotational direction, activates double-threaded tube 146 to concurrently (a) withdraw at least some of the fluid into fluid-retaining chamber 141 from inflatable balloon 22 of balloon-based implant 20, via catheter fluid-conveyance lumen 19, and (b) elongate the length of balloon-based implant 20 (configuration not shown, but equivalent to transitioning back from FIG. 2B to FIG. 2A).

Figure 4B:
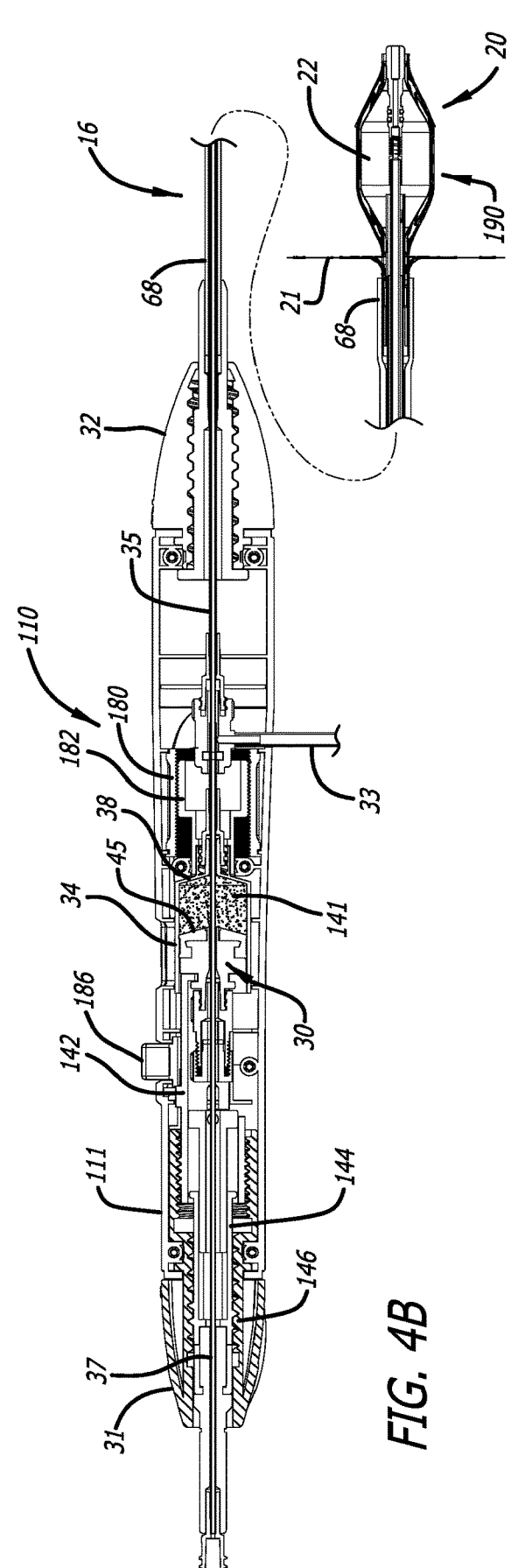
Figures 4C, 4D:
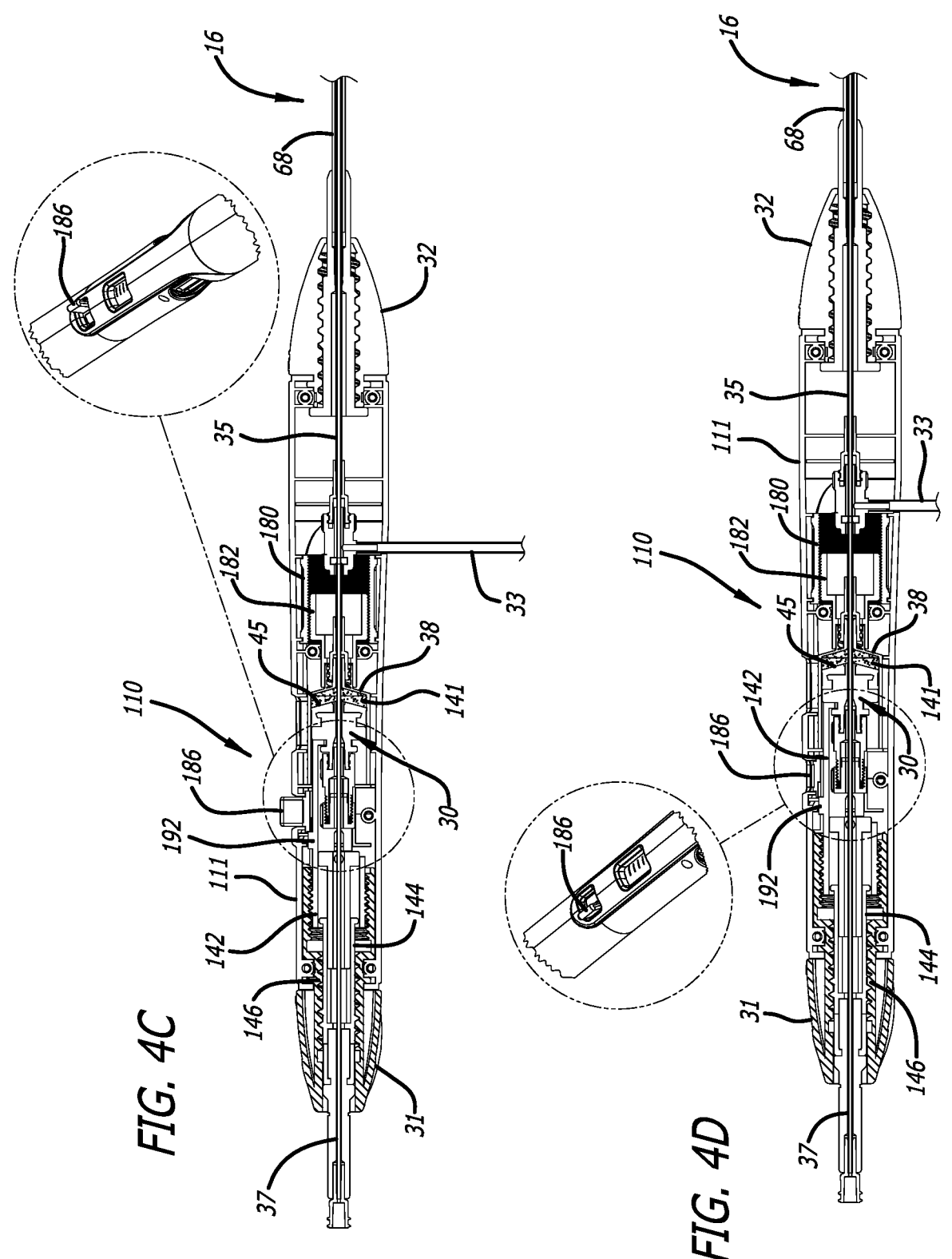
Figures 4E, 4F:
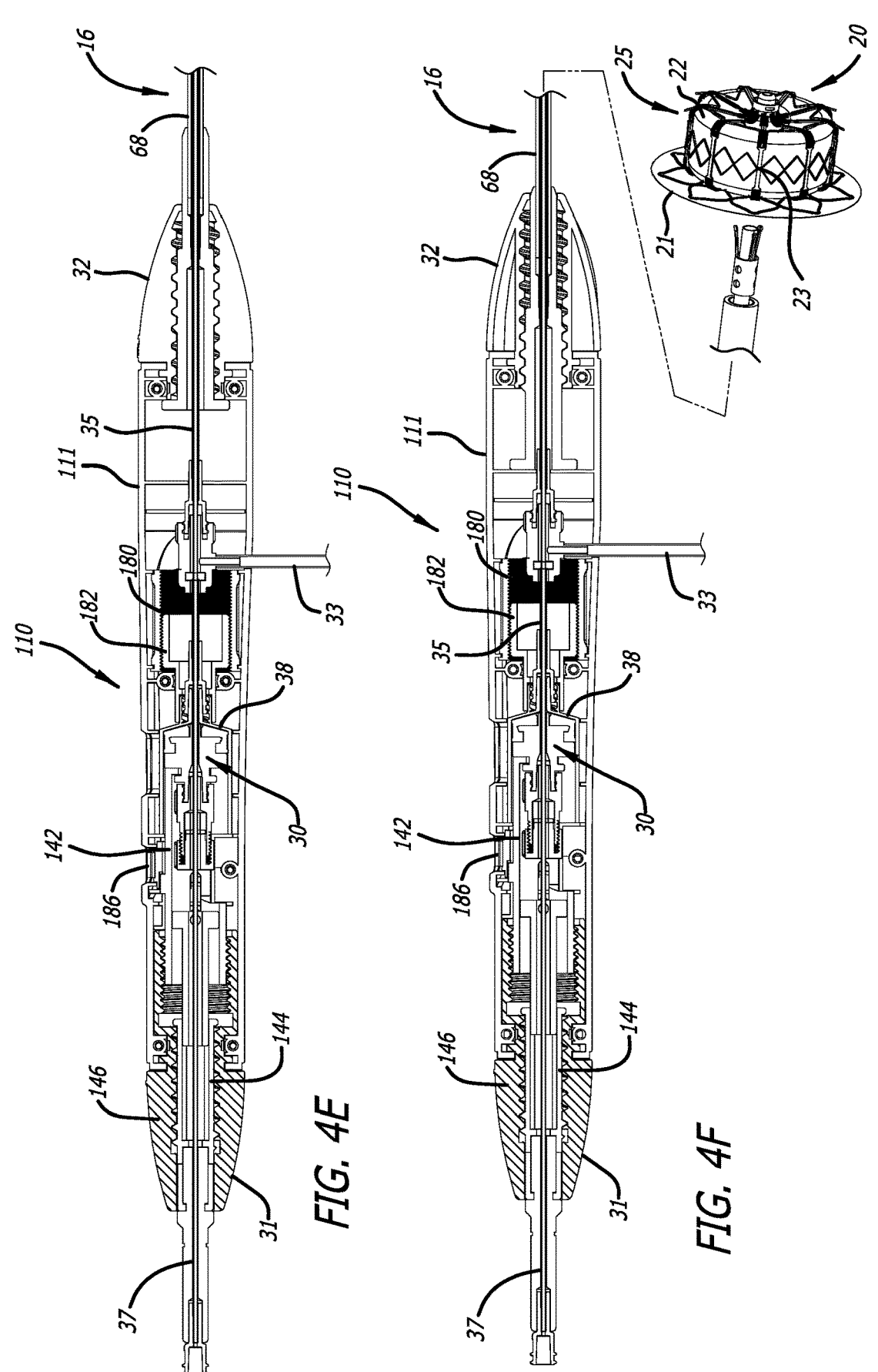

The result of the first transition described immediately above is to cause the distal sliding of distal movable membrane 45 of plunger 30 within fluid-retaining chamber 141 and the fluid inflation of balloon 22 of balloon-based implant 20, concurrently with the shortening of balloon-based implant 20 (e.g., balloon frame 23 thereof), which is connected to actuator 44 via catheter lumen shaft 26 and delivery-handle lumen shaft 37, to bring balloon-based implant 20 to fully-inflated and shortened deployed configuration 25, as shown in FIG. 4F.

FIG. 4B show delivery system 110 after it has been actuated to transition balloon-based implant 20 to a partially-inflated and partially-shortened configuration 190.

For some applications, delivery system 110 is configured to additionally inflate balloon 22 of balloon-based implant 20 without additionally concurrently shortening balloon-based implant 20, such as shown in the transition between FIG. 4B and FIG. 4C.

For some of these applications, delivery handle 111 further comprises a length-maintaining fluid user-control knob 180. Delivery handle 111 is configured such that rotation of length-maintaining fluid user-control knob 180, in a first rotational direction, proximally moves fluid-retaining chamber 141 within delivery handle 111 while plunger 30 remains longitudinally stationary, as shown in the transition between FIG. 4B and FIG. 4C. This relative movement has the effect of expelling additional fluid from fluid-retaining chamber 141 into balloon 22 of balloon-based implant 20, thereby further inflating the balloon. This relative movement is independent of movement of double-threaded tube 146, such that during this further expulsion of fluid and inflation of the balloon, actuator 144 remains stationary and the length of balloon-based implant 20 thus remains constant.

Typically, rotation of length-maintaining fluid user-control knob 180 in a second rotational direction, opposite the first rotation direction, has the opposite effect, namely drawing some of the fluid from balloon 22 back into fluid-retaining chamber 141, without changing a length of balloon-based implant 20.

For example, delivery handle 111 may comprise a length-maintaining fluid actuator 182, which is in threaded communication with length-maintaining fluid user-control knob 180. Rotation of length-maintaining fluid user-control knob 180 in the first rotational direction causes proximal movement of length-maintaining fluid actuator 182, which in turn causes the above-mentioned proximal movement of fluid-retaining chamber 141 within delivery handle 111 while plunger 30 remains longitudinally stationary, as shown in the transition between FIG. 4B and FIG. 4C. Typically, rotation of length-maintaining fluid user-control knob 180 in the second rotational direction has the opposite effect.

For some applications, balloon-based implant 20 is configured such that once it has been shortened to a predetermined length, balloon-based implant 20 becomes irreversibly locked at the predetermined length and a fluid port of the balloon closes, preventing addition or removal of fluid, in order to maintain proper implantation of the implant in the surrounding anatomy, for example using locking mechanism 340, described hereinbelow with reference to FIGS. 6 and 7A-B. Once balloon-based implant 20 become locked, the rotation of proximal rotatable user-control knob 31 in the second rotational direction is no longer possible. However, during the implantation procedure, it may be desired to partially lengthen balloon-based implant 20 and partially unfill balloon 22 thereof in order to reposition or remove the implant before completion of the implantation procedure and/or in order to adjust the implant size to better match a cardiovascular defect. For example, whether it is desired to reposition or remove the implant may be ascertained by injecting contrast medium into lumen entrance 14, through delivery-handle guidewire lumen 29 and catheter guidewire lumen 27, to exit distally to balloon-based implant 20, to visually evaluate by x-ray imaging the balloon-based implant with respect to the surrounding target anatomy.

To this end, in some applications, delivery handle 11 comprises a safety latch 186, which is configured to assume a locked state, such as show in FIGS. 4A-C, and an unlocked state, such as shown in FIGS. 4D-F. The user can transition the safety latch between its two states, typically using a single finger of the user. Typically, the initial state is the unlocked state. When in the locked state, safety latch 186 blocks double-threaded tube 146 from the completion of the concurrent (a) expulsion of the fluid from fluid-retaining chamber 141 into inflatable balloon 22 and (b) shortening of the length of balloon-based implant 20, as described above. Blocking this completion prevents the locking of the implant.

For example, safety latch may limit distal motion of an element of delivery handle 11, such as plunger pusher 142, e.g., a radially-directed tab 192 thereof.

Once safety latch 186 has been transitioned to the unlocked state, such as shown in FIG. 4D, proximal rotatable user-control knob 31 can be further rotated in the first rotation direction to complete the concurrent (a) expulsion of the fluid from fluid-retaining chamber 141 into inflatable balloon 22 and (b) shortening of the length of balloon-based implant 20, as described above, and as can be seen in the transition from FIG. 4D to FIG. 4E.

In addition, if it is desired to introduce additional fluid into balloon 22, such as to achieve greater adherence of balloon-based implant 20 with the surround anatomy, additional fluid may be introduced from cannula extension 33 into delivery-handle fluid-conveyance lumen 28 (distal to fluid-retaining chamber 141) and to balloon 22 of balloon-based implant 20.

Reference is now made to FIGS. 5A-F, which are schematic illustrations of a delivery catheter 216, in accordance with an application of the present invention. Delivery catheter 216 may optionally be used in combination with delivery system 10, described hereinabove with reference to FIGS. 1 and 2A-H, or delivery system 110, described hereinabove with reference to FIGS. 3 and 4A-F. Alternatively, delivery catheter 216 may be used with another delivery system.

Figure 5A:
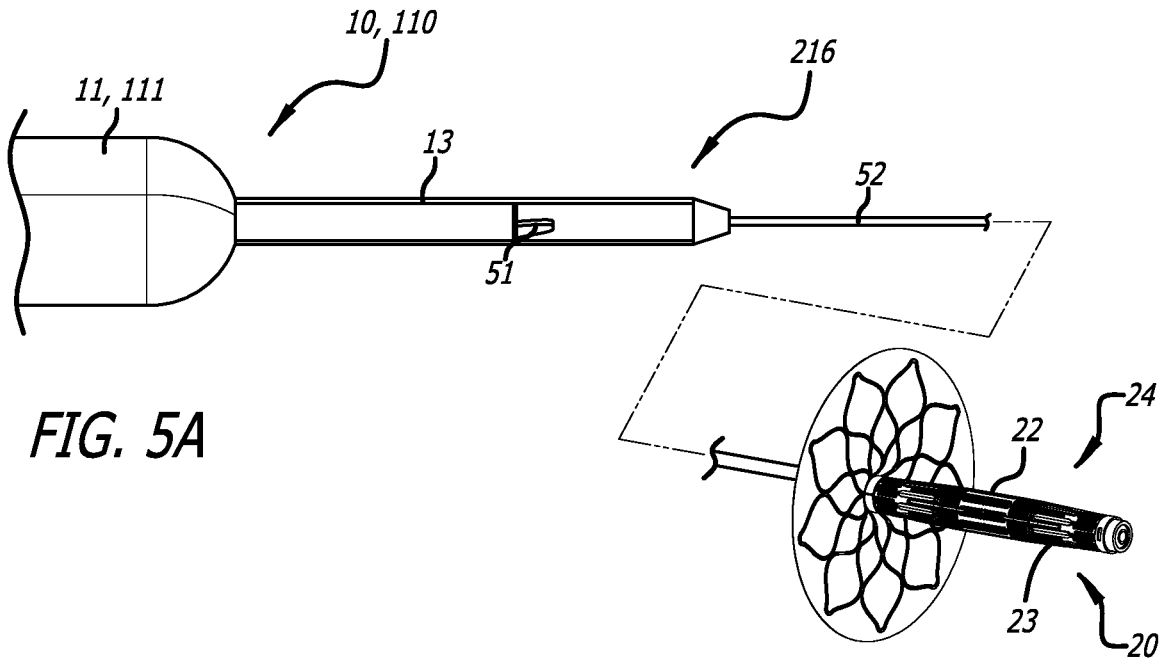

FIG. 5A is a cross-sectional view of delivery catheter 216 with delivery handle 11 and delivery catheter 216 connected to balloon-based implant 20, in a noninflated and non-deployed configuration 24, in accordance with an application of the present invention.

Delivery catheter 216 comprises a double fluid-retaining chamber 13 and an inflation catheter 52 which is directly connected to balloon-based implant 20. Double fluid-retaining chamber 13 is shaped so as to define an opening 51 on its surface, which places in contact the surrounding of delivery catheter 216 with one of two internal sub-chambers of double fluid-retaining chambers 13.

Figure 5B:
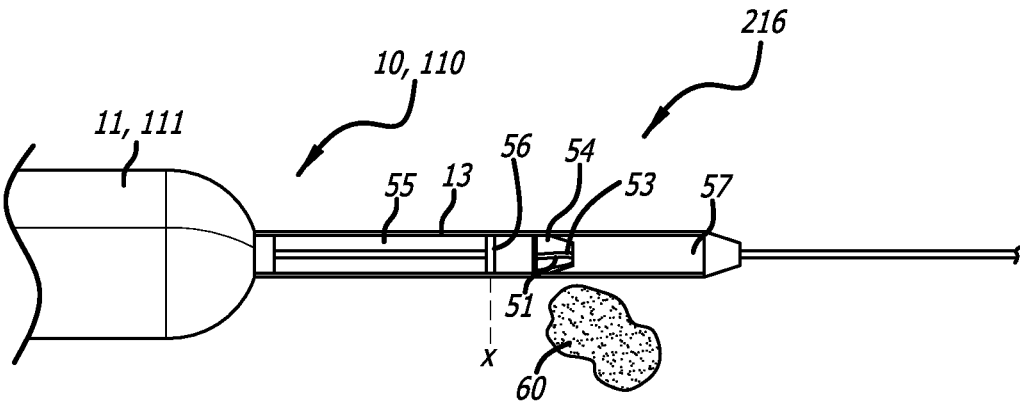

FIG. 5B is a cross-sectional view of delivery catheter 216 showing the inside of double fluid-retaining chamber 13, in accordance with an application of the present invention. The inside of double fluid-retaining chamber 13 is shaped so as to define a proximal chamber 55 and a distal chamber 57.

An opening 51 through the external surface of double fluid-retaining chamber 13 allows the fluid surrounding this opening to enter proximal chamber 55. During a cardiovascular procedure this fluid is blood 60. Opening 51 and double fluid-retaining chamber 13 may be placed equally proximally or distally along delivery catheter 216. Blood 50 can enter proximal chamber 55 only when opening 51 and groove 53 are aligned with each other. A plunger 56 is positioned within proximal chamber 55 and it is placed distally at the beginning of the procedure, at a longitudinal position X.

As shown in FIG. 5C, plunger 56 is retracted proximally to a longitudinal position Y, filling internal fluid proximal chamber 55 with blood 60. The chamber internal volume or wall may be pre-treated with anticoagulant solution to avoid blood clotting within the chamber.

As shown in FIG. 5D, chamber distal end 54 is rotated independently from distal chamber 57, until its groove 53 is in free contact with internal distal chamber 57, occluding by this rotation opening 51 which is located on the external surface of double fluid-retaining chamber 13.

As shown in FIG. 5E, plunger 56 is advanced to distal longitudinal position X, pushing blood 60 from proximal chamber 55 to distal chamber 57 to inflation catheter 52 to balloon-based implant 20. Blood 60 passes through distal chamber 57 to inflate balloon 22 and to conform balloon frame 23. The plunger may be advanced until sufficient inflation is observed with balloon-based implant 20 that transition to a fully inflated and deployed configuration 204. Balloon-based implant 20 may be now detached from delivery catheter 216 and delivery system 10, unless the operator wants to deflate the balloon by retracting the plunger to proximal longitudinal position Y.

FIG. 5F provides a view of delivery system 10 and of the internal components of delivery catheter 216 and of double fluid-retaining chamber 13, in accordance with an application of the present invention.

These steps are reversible and may be used for deflating balloon-based implant 20. These steps may be performed also more than once in series, to provide more inflation volume to balloon-based implant 20.

Figure 6:
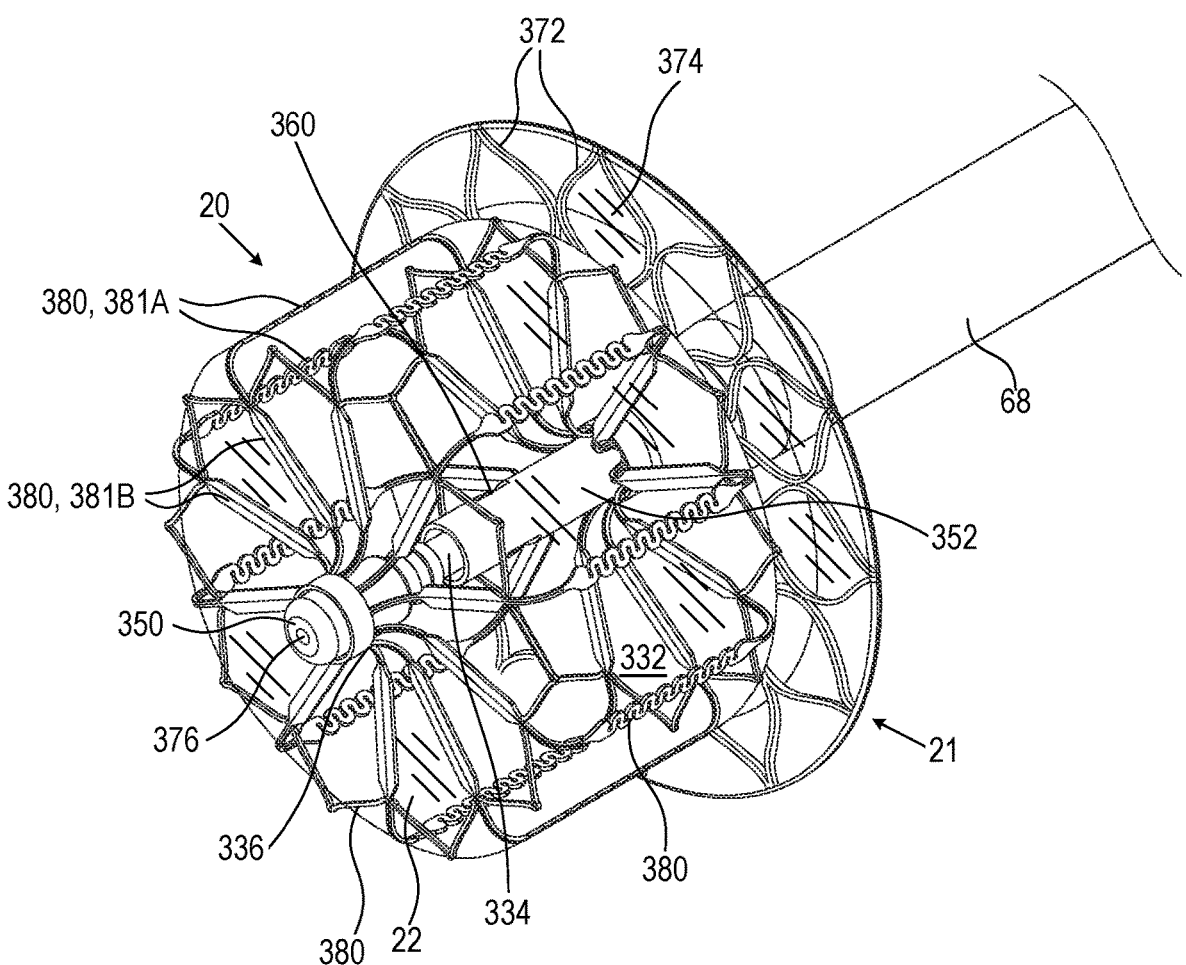
FIG. 6 is a schematic illustration of an occlusion device for occluding a left atrial appendage (LAA), in accordance with an application of the present invention.

FIG. 6 is a schematic illustration of a balloon-based occlusion device 20 for occluding a left atrial appendage (LAA), in accordance with an application of the present invention. Occlusion device 20 may be used with delivery system 10; described hereinabove with reference to FIGS. 1 and 2A-H, delivery system 110, described hereinabove with reference to FIGS. 3 and 4A-F; and/or delivery catheter 216, described hereinabove with reference to FIGS. 5A-F.

Figures 7A, 7B:
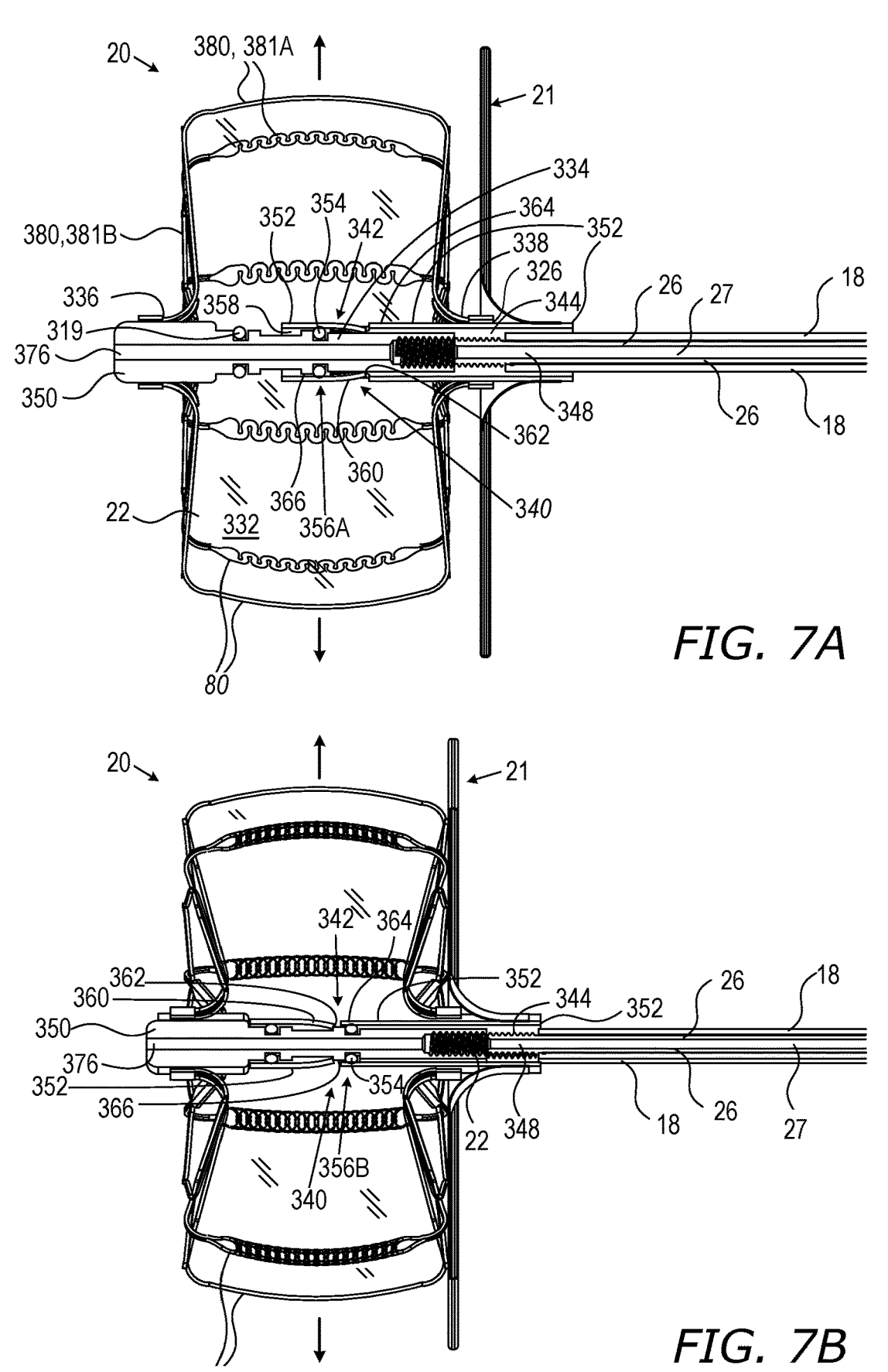
FIGS. 7A-B are schematic cross-sectional illustrations of the occlusion device of FIG. 6 and a distal portion of a delivery system, in accordance with an application of the present invention.

Reference is also made to FIGS. 7A-B, which are schematic cross-sectional illustrations of occlusion device 20 and a distal portion of the delivery system, in accordance with an application of the present invention. FIG. 7A shows occlusion device 20 with a locking mechanism 340 thereof in an unlocked state and a valve 342 thereof in an open state, as described hereinbelow. FIG. 7B shows occlusion device 20 with locking mechanism 340 in a locked state and valve 342 in a closed state, as described hereinbelow.

For some applications, occlusion device 20 comprises:

compliant balloon 22 defining a fluid-tight balloon chamber 332;

an actuating shaft 334, which is (a) disposed at least partially within balloon chamber 332, (b) connected to a distal end portion 336 of balloon 22, and (c) longitudinally moveable with respect to a proximal end portion 338 of balloon 22 so as to set a distance between distal and proximal end portions 336 and 338 of balloon 22;

locking mechanism 340, which is configured to assume locked and unlocked states, as shown in FIGS. 7B and 7A, respectively; and valve 342.

Occlusion device 20 is configured such that proximally longitudinally moving actuating shaft 334 expands balloon 22 in a radial or a lateral direction by shortening the distance between distal and proximal end portions 336 and 338 of balloon 22 to a desired distance.

Locking mechanism 340 is configured, when in the locked state, to maintain, between distal end portion 336 of balloon 22 and proximal end portion 338 of balloon 22, the distance set using actuating shaft 334.

For some applications, occlusion device 20 is shaped so as to define a fluid flow path 344 along (e.g., alongside, as shown) a portion of actuating shaft 334. Valve 342 is configured to selectively:

allow fluid flow between fluid flow path 344 and balloon chamber 332 when valve 342 is in the open state, as shown in FIG. 7A, or block fluid flow between fluid flow path 344 and balloon chamber 332 when valve 342 is in the closed state, as shown in FIG. 7B.

For some applications, occlusion device 20 is configured such that reduction of the distance, by proximal longitudinal movement of actuating shaft 334:

to a first predetermined distance between distal and proximal end portions 336 and 338 of balloon 22 automatically transitions valve 342 from the open state to the closed state, as shown in the transition from FIG. 7A to FIG. 7B, and to a second predetermined distance between distal and proximal end portions 336 and 338 of balloon 22 automatically transitions locking mechanism 340 from the unlocked state to the locked state, as also shown in the transition from FIG. 7A to FIG. 7B.

For some applications, the first predetermined distance does not equal the second predetermined distance. For example, the first predetermined distance may be less than the second predetermined distance, such that the proximal longitudinal movement of actuating shaft 334 first automatically transitions valve 342 from the open state to the closed state and subsequently automatically transitions locking mechanism 340 from the unlocked state to the locked state. Alternatively, the first predetermined distance may be greater than the second predetermined distance, such that this sequence is reversed.

Further alternatively, for some applications, the first predetermined distance equals the second predetermined distance, such that the proximal longitudinal movement of actuating shaft 334 simultaneously automatically transitions valve 342 from the open state to the closed state and automatically transitions locking mechanism 340 from the unlocked state to the locked state.

As described hereinabove, in order to cause the above-mentioned proximal longitudinal movement of actuating shaft 334, the delivery system comprises a catheter lumen shaft 26, which is releasably coupled a proximal end portion of actuating shaft 334. For example, a distal portion of catheter lumen shaft 26 may comprise a pull-shaft coupling 348, which may, for example, be shaped so as to define a thread that removably engages a corresponding thread defined by the proximal end portion of actuating shaft 334. Rotation of catheter lumen shaft 26 disengages shaft coupling 348 from the corresponding thread defined by the proximal end portion of actuating shaft 334.

Occlusion device 20 is configured to be releasably connected to the delivery system. Occlusion device 20 is configured such that fluid flow path 344 is coupled in fluid communication with the delivery system when occlusion device 20 is releasably connected to the delivery system, such as shown in FIGS. 7A-B.

For some applications, actuating shaft 334 is shaped so as to define, at least in part, a distal tip 350 disposed at distal end portion 336 of balloon 22, as shown in FIGS. 6 and 7A-B.

For some other applications, occlusion device 20 further comprises a distal tip disposed at distal end portion 336 of balloon 22, and actuating shaft 334 is connected to the distal tip (configuration not shown).

Alternatively or additionally, for some applications, occlusion device 20 further comprises a proximal base disposed at proximal end portion 338 of balloon 22, and actuating shaft 334 is moveable (e.g., longitudinally or rotationally) with respect to the proximal base (configuration not shown).

For some applications, valve 342 is disposed along actuating shaft 334, such as shown in FIGS. 7A-B.

For some applications, occlusion device 20 further comprises a proximal tube 352, which is axially fixed with respect to proximal end portion 338 of balloon 22. Actuating shaft 334 is slidably disposed partially within proximal tube 352, e.g., so as to indirectly connect actuating shaft 334 to proximal end portion 338 via proximal tube 352. For some of these applications, occlusion device 20 is shaped so as to define fluid flow path 344 along the portion of actuating shaft 334, radially between an external surface of actuating shaft 334 and an internal surface of proximal tube 352, such as shown in FIGS. 7A-B. Optionally, valve 342 is disposed along actuating shaft 334.

For some applications, valve 342 comprises a seal 354 around at least a portion of (e.g., entirely around) the external surface of actuating shaft 334. Valve 342 is configured to assume (a) the open state when seal 354 is disposed at one or more first axial positions 356A with respect to proximal tube 352 (one such first axial position is shown in FIG. 7A), and (b) the closed state when seal 354 is disposed at one or more second axial positions 356B with respect to proximal tube 352 (one such second axial position is shown in FIG. 7B). The one or more second axial positions 356B are proximal to the one or more first axial positions 356A. For example, seal 354 may comprise an O-ring, as shown in FIGS. 7A-B, e.g., a single O-ring or a series of O-rings. Optionally, one or more additional seals 319, e.g., one or more O-rings, are provided to provide further stabilization an alignment of the distal tube inside the proximal tube by friction.

For some applications, seal 354, actuating shaft 334, and proximal tube 352 are arranged such that seal 354 blocks fluid flow out of a distal end 358 of proximal tube 352, at least when seal 354 is disposed at the one or more first axial positions 356A with respect to proximal tube 352, such as shown in FIG. 7A. Alternatively or additionally, friction between seal 354 and the inner surface of proximal tube 352 increases structural stability, and/or enables stepwise inflation/implantation.

For some applications, a wall of proximal tube 352 is shaped so as to define one or more tabs 360 through the wall. The one or more tabs 360 are biased to flex radially inward. When valve 342 is in the open state, as shown in FIG. 7A, fluid flow path 344 passes through the wall between respective proximal ends 362 of the one or more tabs 360 and a non-tabbed portion 364 of the wall axially adjacent the one or more tabs 360, such as proximal to the one or more tabs 360, as shown.

For some applications, the external surface of actuating shaft 334 is shaped so as to define one or more protrusions 366 around at least a portion of (e.g., entirely around) actuating shaft 334. Proximal ends 362 of the one or more tabs 360 are shaped so as to prevent distal movement of the one or more protrusions 366 when the one or more protrusions 366 are disposed proximal to the proximal ends 362 of the one or more tabs 360, such as shown in FIG. 7B, thereby causing locking mechanism 340 to assume the locked state.

Figures 8A, 8B:
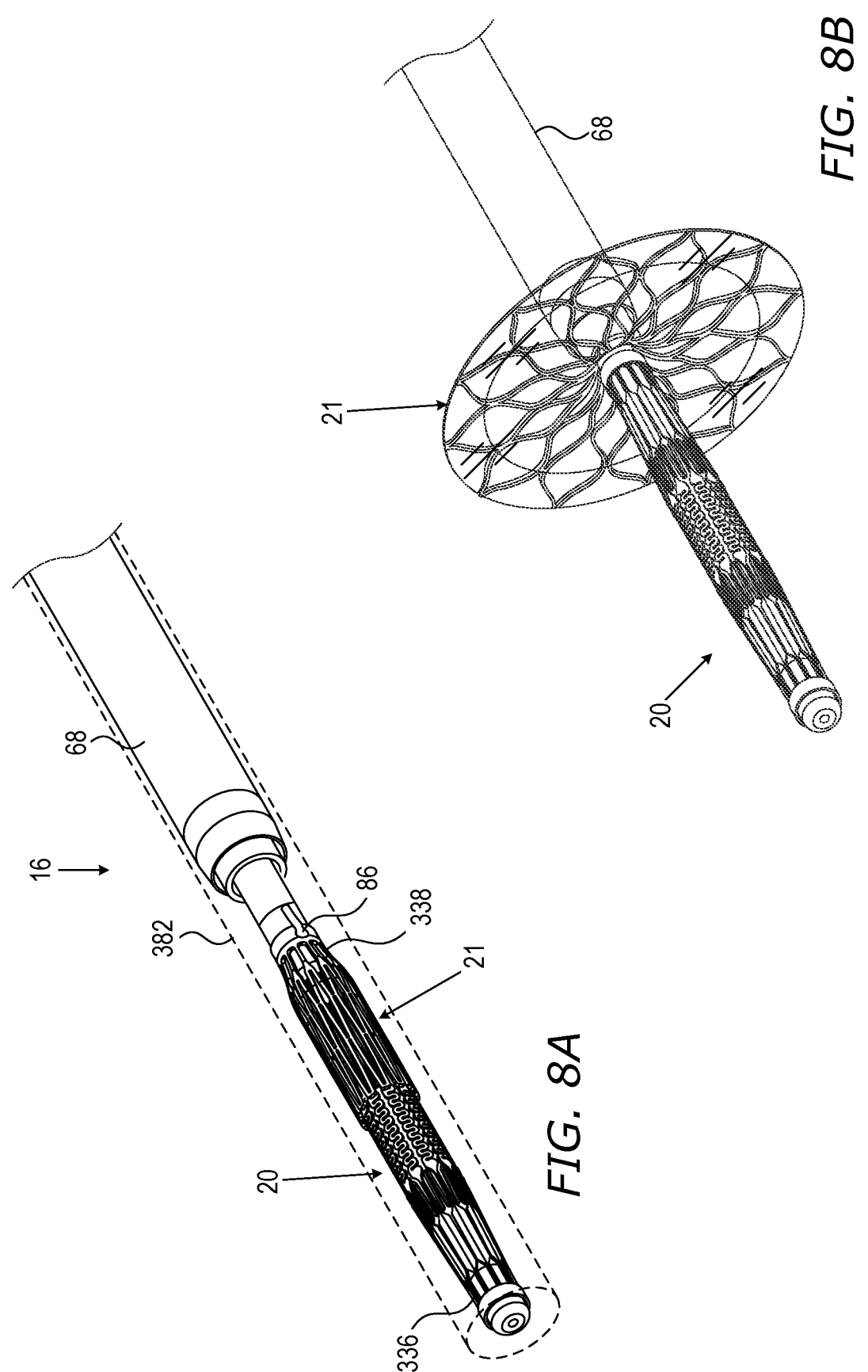
FIGS. 8A-F are schematic illustrations of steps of a method of deploying the occlusion device of FIG. 6 using the delivery system of FIGS. 7A-B, in accordance with an application of the present invention.

For some applications, occlusion device 20 further comprises a proximal LAA-orifice cover 21, which:

is fixed to proximal tube 352 radially surrounding proximal tube 352, is configured to assume a radially-compressed state, such as shown in FIG. 8A, described hereinbelow, and a radially-expanded state, such as shown in FIGS. 6 and 7A-B, comprises frame 372 and a covering 374 fixed to frame 372, when in the radially-expanded state, is generally orthogonal to proximal tube 352 and has a greatest dimension, measured perpendicular to proximal tube 352, of at least 20 mm (e.g., at least 20 mm), no more than 50 mm (e.g., no more than 30 mm), and/or between 20 and 50 mm (e.g., between 20 and 30 mm), and is typically indirectly connected to balloon 22 via proximal tube 352 and is not directly connected to balloon 22.

This indirect connection of proximal LAA-orifice cover 21 to balloon 22 generally prevents an anodic reaction between the typically super-elastic (e.g., Nitinol) material of frame 372 of proximal LAA-orifice cover 21 and the typically plastically deformable (e.g., stainless steel) material of struts 380, described hereinbelow. Such a reaction might have occurred if the two elements were instead welded or otherwise bonded together in contact with each other. (Connection of the elements via an independent and passive element, such as an internal tube or shaft, also does not cause such a reaction.) Alternatively, proximal LAA-orifice cover 21 is directly connected to balloon 22, such as if frame 372 comprises a different plastically-deformable material, such as titanium.

For some applications, occlusion device 20 further comprises orifice-support stent 290, described hereinbelow with reference to FIGS. 8 and 9A-B.

For some applications, actuating shaft 334 is shaped so as to define a guidewire lumen 376 for slidingly receiving therein a guidewire and/or passage of fluid injected under pressure, such as contrast media injected from the proximal handle of the delivery tool to the distal end of the occlusion device. Alternatively, for other applications, actuating shaft 334 is not shaped so as to define a guidewire lumen.

For some applications, compliant balloon 22 comprises a compliant material selected from the group consisting of: polycaprolactone (PCL), polyglycolic acid (PGA), polylactic acid (PLA), and polydioxanone (PDO or PDS), silicone, polyurethane, polytetrafluoroethylene (PTFE), polymethylmethacrylate, polyether ether ketone (PEEK), polyvinyl chloride, polyethylene terephthalate, nylon, polyamide, polyamide, and polyether block amide (PEBA).

For some applications, balloon 22 has an average wall thickness of between 100 and 5000 microns. Alternatively or additionally, for some applications, balloon 22 has, at a thinnest portion of a wall of balloon 22, a thinnest wall thickness of between 20 and 500 microns.

For some applications, occlusion device 20 further comprises connecting struts 380 fixed to distal end portion 336 of balloon 22 and to proximal end portion 338 of balloon 22. Struts 380 may be disposed inside balloon 22, outside balloon 22, or some inside and some outside balloon 22. For some applications, struts 380 are arranged as a frame. For some applications, struts 380 are arranged in a cage-like arrangement. Typically, struts 380 comprise a plastically-deformable material, such as stainless steel or titanium. Typically, struts 380 help shape balloon 22 as the balloon chamber is inflated and/or the balloon is shortened.

Typically, occlusion device 20 is configured such that inflation of balloon chamber 332 plastically deforms connecting struts 380. For some applications, occlusion device 20 is configured such that shortening of balloon 22 plastically deforms connecting struts 380.

For some applications, struts 380 are configured such that inflation of balloon chamber 332 primarily causes radial deformation of struts 380, rather than deformation of the struts in a distal or proximal direction. To this end, first lateral portions 381A of struts 380 arranged along a lateral surface of balloon 22 may be more compliant than second end portions 381B of struts 380 arranged on a distal surface of balloon 22 and/or on a proximal surface of balloon 22. For example, first lateral portions 381A may be thinner than second end portions 381B, as shown in FIG. 6, and/or first lateral portions 381A may be shaped to be more compliant, e.g., have a serpentine (e.g., sinusoidal) shape, as shown. Typically, first lateral portions 381A are oriented parallel to a central longitudinal axis of occlusion device 20.

Reference is now made to FIGS. 8A-F, which are schematic illustrations of steps of a method of deploying occlusion device 20 using the delivery system, in accordance with an application of the present invention.

Figure 8C:
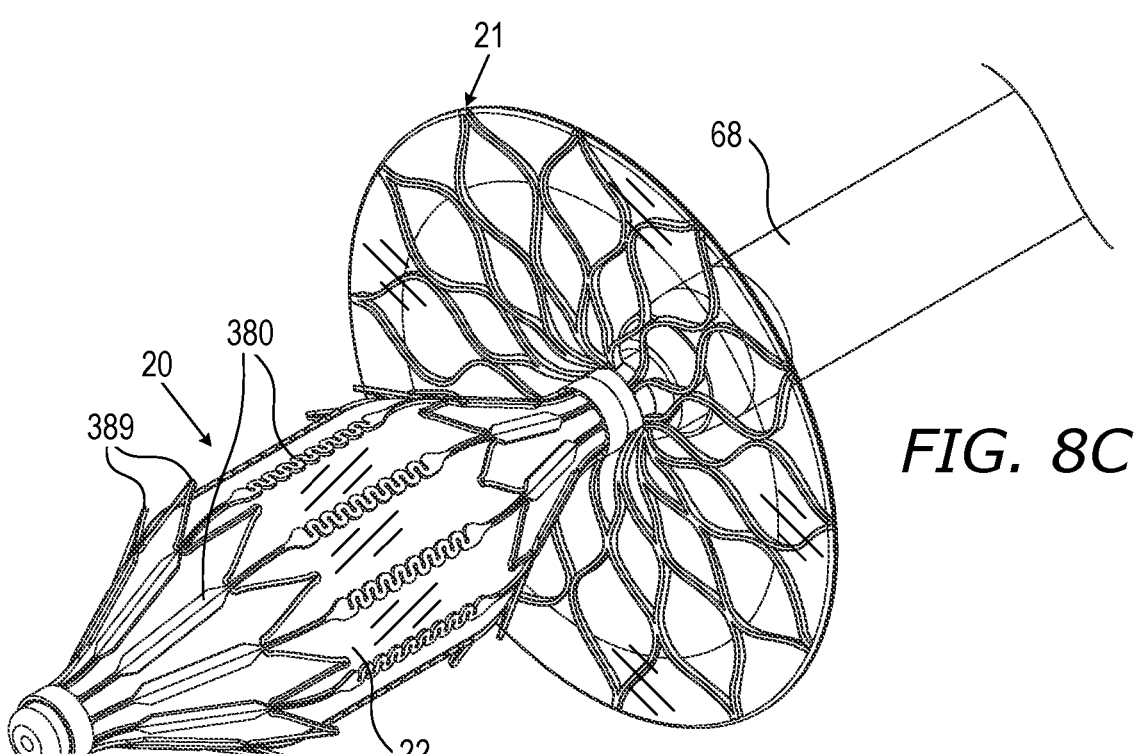
Figure 8D:
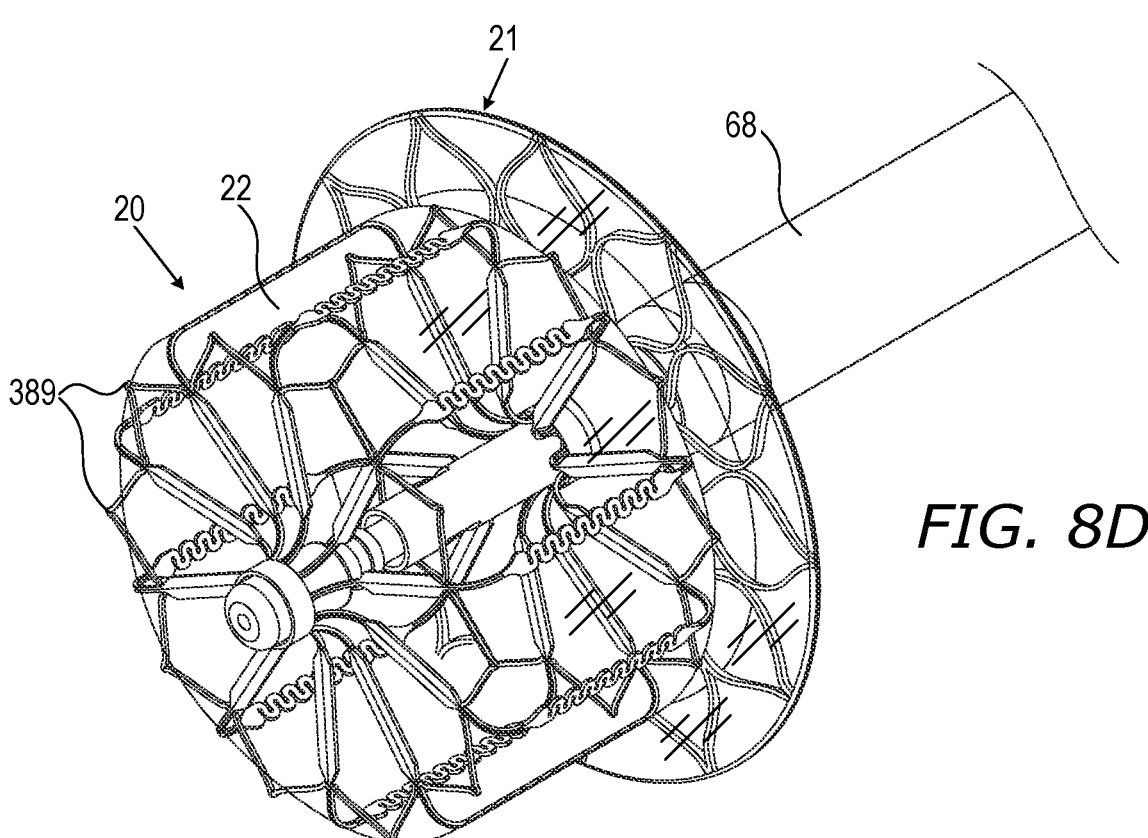
Figure 8E:
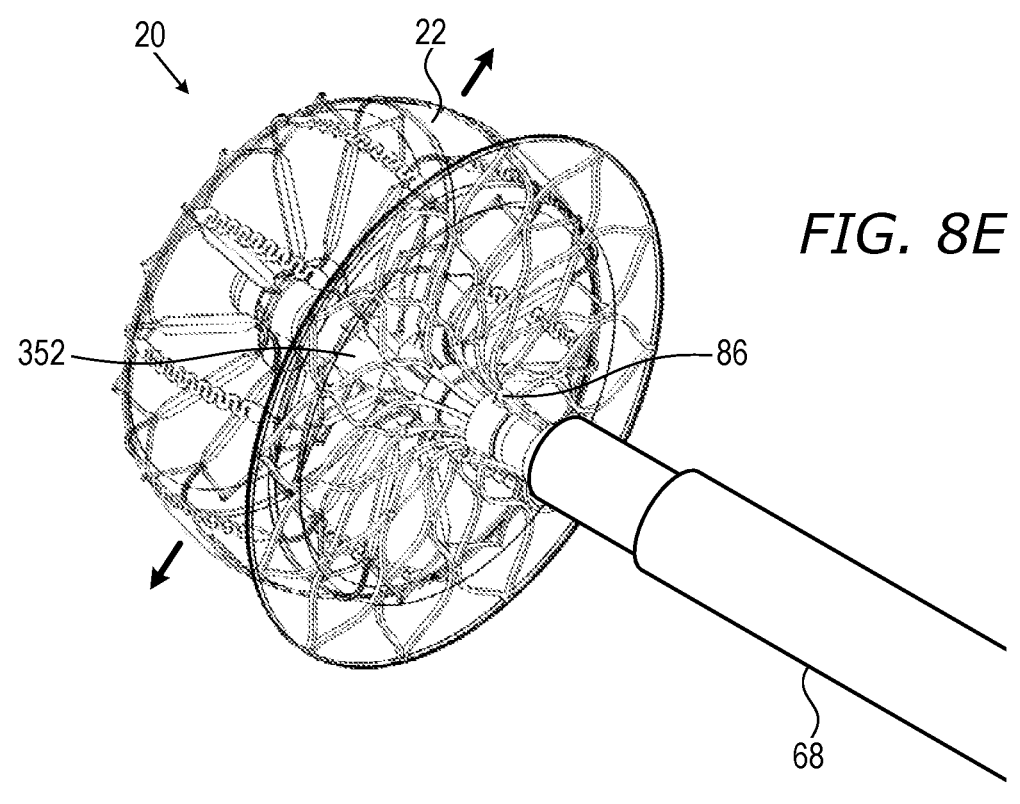
Figure 8F:
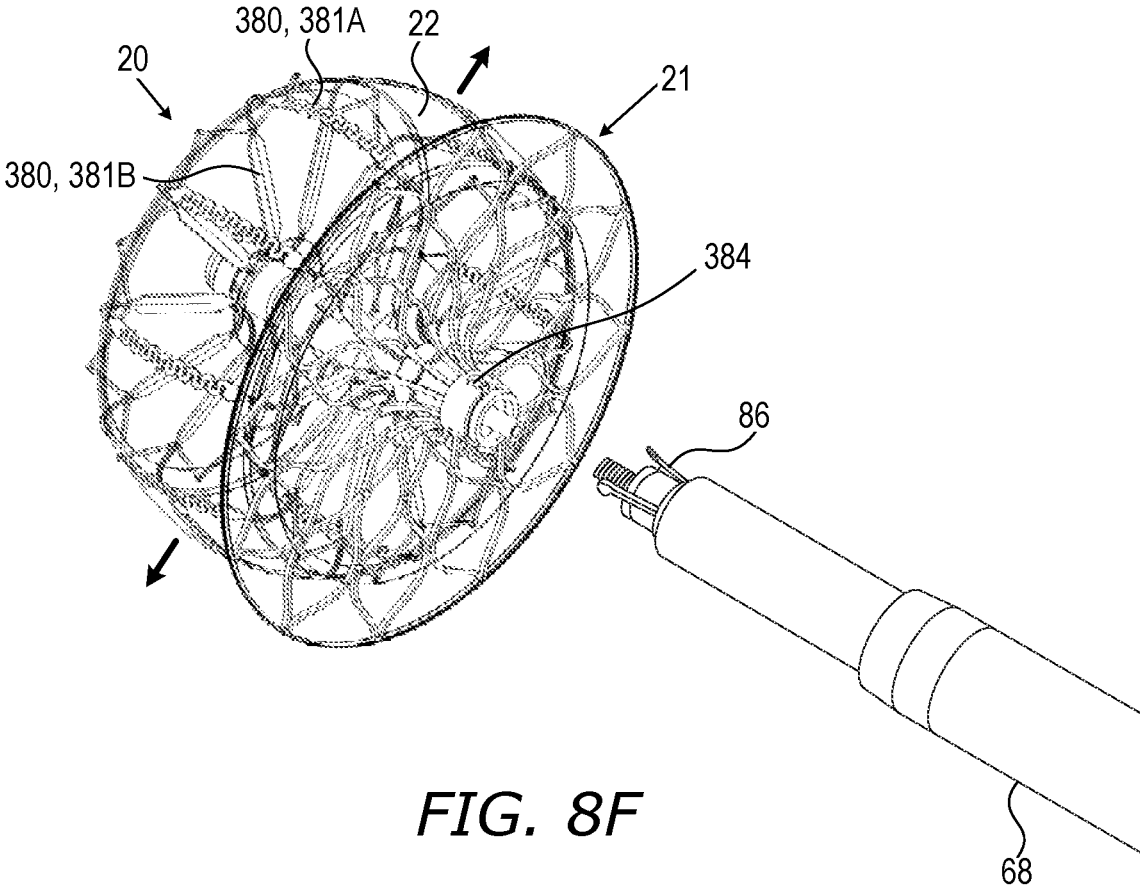
Figures 9A, 9B:
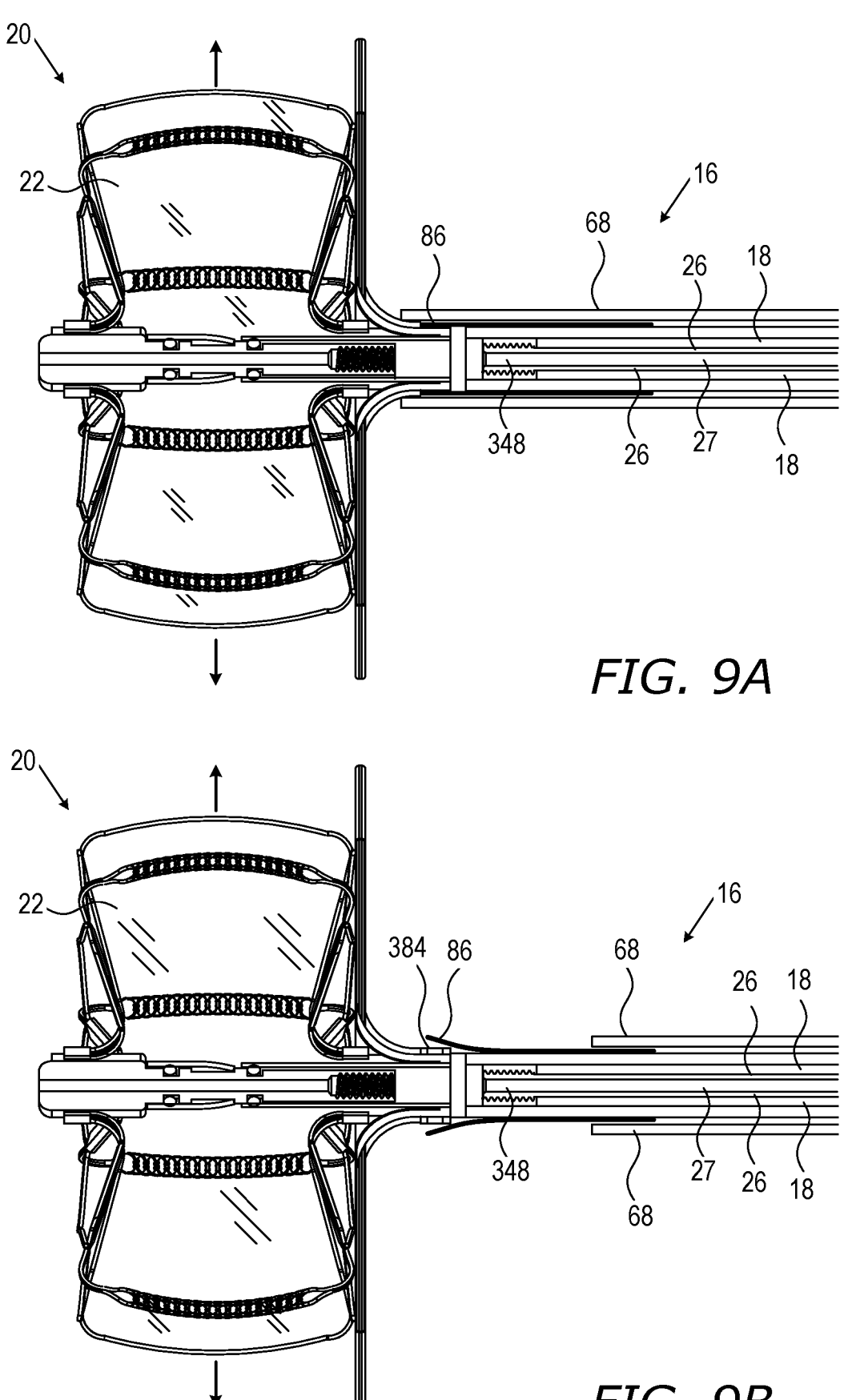
FIGS. 9A-C are schematic cross-sectional views of a portion of the steps of the method shown in FIGS. 8A-F, in accordance with an application of the present invention.
Figure 9C:
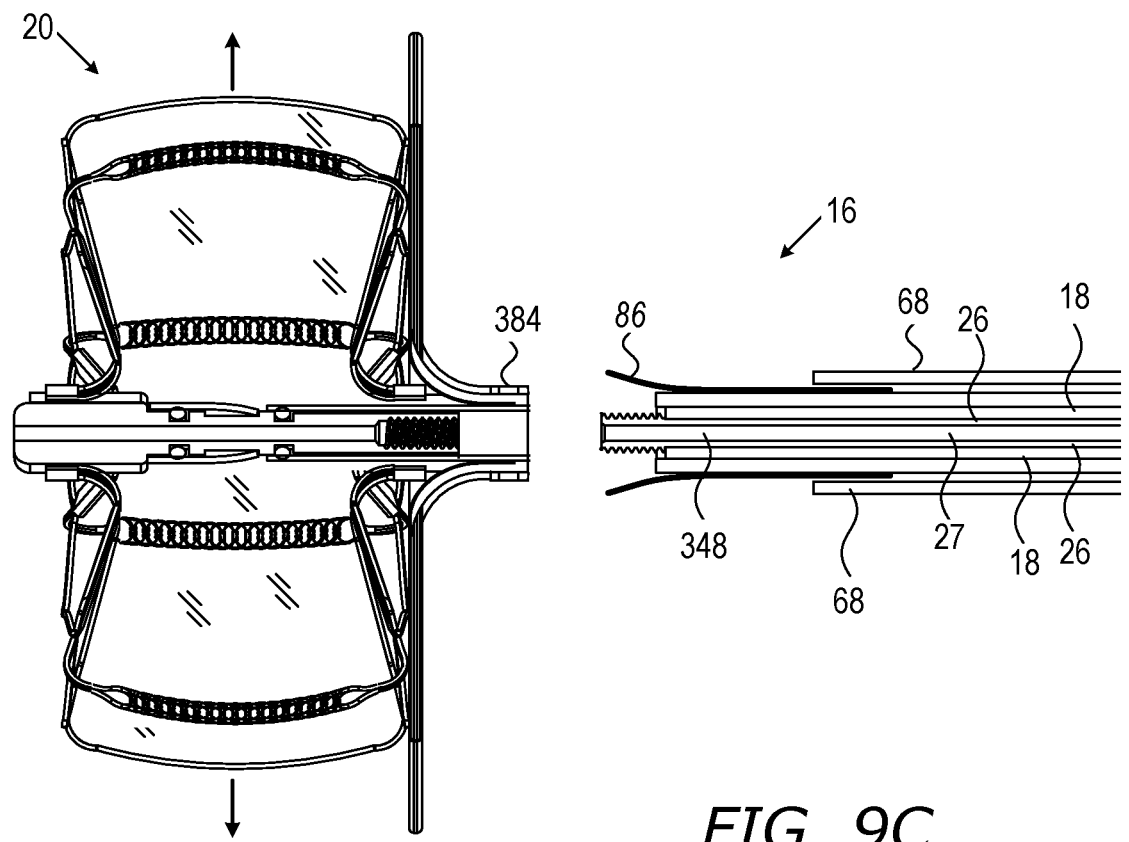
Figure 10:
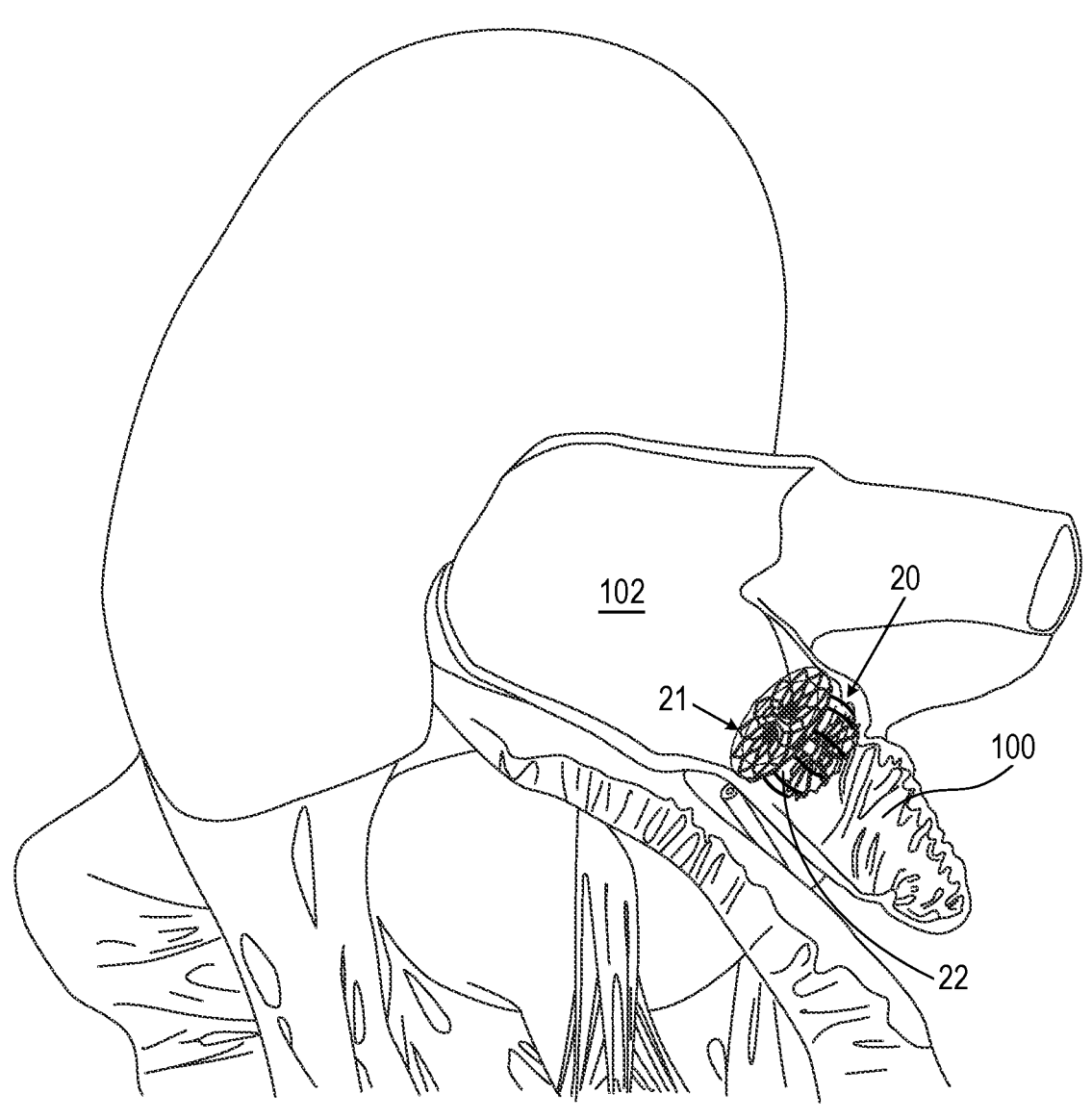
FIG. 10 is a schematic illustration of the occlusion device of FIG. 6 implanted to occlude an LAA, in accordance with an application of the present invention.

Reference is also made to FIGS. 9A-C, which are schematic cross-sectional views of a portion of the steps of the method shown in FIGS. 8A-F, in accordance with an application of the present invention.

FIG. 8A schematically shows occlusion device 20 releasably disposed in a radially-compressed state within a sheath 382 of the delivery system. Typically, a greatest distance between proximal end portion 338 of balloon 22 and distal end portion 336 of balloon 22 is at least 8 mm (e.g., at least 15 mm), no more than 80 mm (e.g. no more than 60 mm), and/or between 8 and 80 mm (e.g., between 15 and 60 mm), when occlusion device 20 is in this radially-compressed state.

For some applications, occlusion device 20 comprises a proximal connector 384 that is configured to releasably connect occlusion device 20 to a correspondingly configured distal connector 86 of the delivery system, such as described hereinabove with reference to FIG. 2H.

For some applications, distal connector 86 comprises one or more legs that engage one or more respective coupling sites (e.g., slots) of proximal connector 384, such as perhaps best seen in FIGS. 9A-C. For example, the legs may be configured to biased radially outward when in an unconstrained, resting state, and may be held radially inward engaging the coupling sites of proximal connector 384, such as by outer implant-coupling tube 68, as shown in FIG. 9A. Proximal withdrawal of outer implant-coupling tube 68 with respect to occlusion device 20 release the legs, as shown in FIG. 9B.

Alternatively, proximal connector 384 is shaped so as to define a thread (configuration not shown).

FIG. 8B shows occlusion device 20 after sheath 382 has been proximally withdrawn, thereby releasing occlusion device 20. FIG. 8B also shows proximal LAA-orifice cover 21 in its radially-expanded state. Typically, frame 372 of proximal LAA-orifice cover 21 comprises a shape-memory memory, e.g., a super-elastic metal, which causes cover 21 to automatically transition to the radially-expanded state upon release from sheath 382. Balloon 22 remains in a non-inflated, elongate configuration at this stage of deployment.

Typically, a healthcare worker places the distal end of occlusion device 20 into the LAA, using delivery system navigation.

As shown in FIGS. 8C-D, the healthcare worker inflates balloon chamber 332. FIG. 8C shows occlusion device 20 upon partial inflation of balloon chamber 332, while FIG. 8D shows occlusion device 20 upon complete inflation of balloon chamber 332. Balloon 22 may be inflated by filling balloon chamber 332 with any fluid, including but not limited to saline solution (optionally comprising a contrast medium), blood (e.g., autologous blood), foam, and/or a glue (e.g., a gel, a liquid polymer that can change its proprieties to become rigid, or a hydrogel that remains a gel or self-cures at body temperature).

For some applications, struts 380 are shaped so as to define a plurality of spikes 389 that are initially generally axially oriented, as shown in FIG. 8C, and are configured to extend more radially upon expansion of balloon 22 to serve as tissue-engaging barbs, as shown in FIG. 8D.

FIGS. 8E and 9A show occlusion device 20 after (a) valve 342 has transitioned from the open state to the closed state, (b) actuating shaft 334 has been proximally longitudinally moved to expand balloon 22 in a radial or a lateral direction by shortening the distance between distal and proximal end portions 336 and 338 of balloon 22 to a desired distance, and (c) locking mechanism 340 has transitioned from the unlocked state to the locked state, as described hereinabove with reference to FIGS. 7A-B. Typically, after balloon 22 has been finally filled, actuating shaft 334 is proximally longitudinally moved to expand balloon 22 in a radial or a lateral direction by shortening the distance between distal and proximal end portions 336 and 338 of balloon 22 to a desired distance. Proximal connector 384 of occlusion device 20 is still releasably connected to correspondingly configured distal connector 86 of the delivery system.

FIGS. 8F and 9B-C show occlusion device 20 after proximal connector 384 of occlusion device 20 has been released from distal connector 86 of the delivery system.

FIG. 9C also shows occlusion device 20 after catheter lumen shaft 26 has been decoupled from the proximal end portion of actuating shaft 334, such as by rotating catheter lumen shaft 26 to unscrew it, as described hereinabove.

Reference is now made to FIG. 20, which is a schematic illustration of occlusion device 20 implanted to occlude an LAA 100, in accordance with an application of the present invention. As can be seen, balloon 22 is disposed within LAA 100, and proximal LAA-orifice cover 21 is disposed in a left atrium 102 outside LAA 100, against the atrial wall surrounding the orifice of LAA 100, thereby creating a continuum with the atrium at the LAA level. Typically, proximal LAA-orifice cover 21 protrudes only minimally because of its relatively flat shape, so as not to interfere with blood flow and not to cause thrombosis. Typically, struts 380 provide most of the anchoring of occlusion device 20, and balloon 22 provides most of the sealing of the LAA. In addition, in configurations in which covering 374 of proximal LAA-orifice cover 21 is blood-impermeable, proximal LAA-orifice cover 21 provides additional sealing of the LAA, primarily to inhibit creation of thrombi on the balloon surface at the orifice level.

For some applications, proximal LAA-orifice cover 21 is asymmetric about proximal tube 352, e.g., elliptical or with a radius greater in one direction than in the perpendicular direction.

For some applications, proximal LAA-orifice cover 21 is configured to have an adjustable greatest dimension measured perpendicular to proximal tube 352. For example, rotation of a proximal LAA-orifice cover 21 adjustment mechanism may adjust the greatest dimension.

For some applications, covering 374 of proximal LAA-orifice cover 21 is blood-permeable, so as to serve as filter for the passage of blood in and out of the LAA. For other applications, covering 374 is not blood-permeable, so as to create a secondary sealing of the LAA in addition to the sealing provided by balloon 22.

For some applications, proximal LAA-orifice cover 21 is bioresorbable and/or drug-eluting.

For some applications, occlusion device 20 is implanted to treat paravalvular leak, for example as described in FIGS. 13A-B of PCT Publication WO 2020/060587 to Maisano et al., which is incorporated herein by reference.

In the context of the present disclosure, the terms "distal" and "proximal" are used accordingly to their standard meaning in the field of percutaneous cardiovascular devices. The term "proximal" refers to those components of the device assembly which, when following a delivery catheter during percutaneous delivery, are closer to the end of the catheter that is configured for manipulation by the user (e.g., a delivery handle manipulated by a physician). The term "distal" is used to refer to those components of the device assembly that are more distant from the end of the catheter that is configured for manipulation by the user and/or that are inserted farther into the body of a patient.

The term "compliant" used herein in relation with balloons or with structural components implies a deformability that substantially follows an applied force. Accordingly, a "compliant balloon" means a balloon which progressively expands under the effect of increasing radial pressure as long as a certain burst pressure is not exceeded.

As used herein, the term "strut" means an elongate structural element which can be formed, e.g., a thin wire, rod, or thick-walled tube, all of which do not necessarily have a circular cross section.

In an embodiment, the techniques and apparatus described herein are combined with techniques and apparatus described in one or more of the following patent applications, which are assigned to the assignee of the present application and are incorporated herein by reference:

European Patent Application Publication EP 3 459 469 A1 to Maisano et al.;

PCT Publication WO 2019/057950 to Maisano et al.;

US Patent Application Publication 2020/0275935 to Maisano et al.;

PCT Publication WO 2020/060587 to Maisano et al.;

U.S. application Ser. No. 17/207,074, filed Mar. 10, 2021, which published as US Patent Application Publication 2021/0204961 to Maisano et al.;

U.S. Provisional Application 62/906,393, filed Sep. 26, 2019;

International Application PCT/IL2020/051041, filed Sep. 24, 2020, which published as PCT Publication WO 2021/059273 to Guidotti et al.; and/or U.S. Provisional Application 62/994,465, filed Mar. 25, 2020.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A delivery system for delivering and deploying an implantable balloon-based occlusion device that includes an inflatable balloon, the delivery system comprising:
   a delivery handle, which comprises:
      a fluid-retaining chamber, delimited by a tubular barrel having a proximal end, a distal end, and an internal surface;
      a plunger, which is slidingly disposed in the fluid-retaining chamber so as to provide a movable membrane; and
      a proximal rotatable user-control knob;
   a fluid-conveyance lumen catheter, which is shaped so as to define a catheter fluid-conveyance lumen in fluid communication (a) with the fluid-retaining chamber and (b) with the inflatable balloon of the balloon-based occlusion device when the fluid-conveyance lumen catheter is coupled to the inflatable balloon; and
   a catheter lumen shaft, which is configured to be in reversible connection with the balloon-based occlusion device, longitudinally slidable with respect to the delivery handle,
   wherein the delivery handle is configured such that rotation of the proximal rotatable user-control knob in a first rotational direction concurrently (a) expels at least some of the fluid from the fluid-retaining chamber into the inflatable balloon of the balloon-based occlusion device, via the catheter fluid-conveyance lumen, and (b) shortens a length of the balloon-based occlusion device by proximally pulling the catheter lumen shaft.

2. The delivery system according to claim 1, wherein the delivery handle is configured such that rotation of the proximal rotatable user-control knob in a second rotational direction opposite the first rotational direction concurrently (a) withdraws at least some of the fluid into the fluid-retaining chamber from the inflatable balloon of the balloon-based occlusion device, via the catheter fluid-conveyance lumen, and (b) elongates the length of the balloon-based occlusion device by distally pushing the catheter lumen shaft.

3. The delivery system according to claim 1, wherein the catheter lumen shaft is disposed within the catheter fluid-conveyance lumen.

4. The delivery system according to claim 1, wherein the fluid-retaining chamber is disposed within the delivery handle.

5. The delivery system according to claim 1, wherein the delivery handle further comprises a distal user control, which is configured to release the balloon-based implant from the delivery system.

6. The delivery system according to claim 1, wherein the delivery handle comprises a window opening, and wherein an external surface of the fluid-retaining chamber is marked with a scale that is visible through the window opening, to enable a user to monitor an amount of the fluid present within the fluid-retaining chamber.

7. The delivery system according to claim 1, wherein the delivery handle comprises a delivery-handle fluid-conveyance lumen tube, which is shaped so as to define a delivery-handle fluid-conveyance lumen in fluid communication with the fluid-retaining chamber and the catheter fluid-conveyance lumen.

8. The delivery system according to claim 7, wherein the delivery handle comprises a delivery-handle lumen shaft, which is disposed within the delivery-handle fluid-conveyance lumen, and which extends from the catheter lumen shaft and longitudinally slidable with respect to the delivery handle.

9. The delivery system according to claim 1, further comprising a cannula extension, having one end thereof which is connected at one end of the cannula extension in fluid communication with the fluid-retaining chamber.

10. The delivery system according to claim 1, wherein the delivery handle further comprises a length-maintaining fluid user-control knob, and wherein the delivery handle is configured such that rotation of the length-maintaining fluid user-control knob, in a first rotational direction, proximally moves the fluid-retaining chamber within the delivery handle while the plunger remains longitudinally stationary, thereby expelling additional fluid from the fluid-retaining chamber into the balloon of the balloon-based implant without changing the length of the balloon-based occlusion device.

11. The delivery system according to claim 1, wherein the delivery handle further comprises a double-threaded tube, which is connected to the proximal rotatable user-control knob, and which connects and couples actuation of the plunger into the fluid-retaining chamber and longitudinal sliding of the catheter lumen shaft.

12. The delivery system according to claim 11,
wherein the delivery handle further comprises an actuator, connected to the catheter lumen shaft, and
wherein the delivery handle is configured such that rotation of the proximal rotatable user-control knob in the first rotational direction activates the double-threaded tube to concurrently (a) expel at least some of the fluid from the fluid-retaining chamber into the inflatable balloon of the balloon-based occlusion device, via the catheter fluid-conveyance lumen, and (b) shorten the length of the balloon-based occlusion device by proximally moving the actuator, which in turn proximally pulls the catheter lumen shaft.

13. The delivery system according to claim 12, wherein the delivery handle is configured such that rotation of the proximal rotatable user-control knob in a second rotational direction opposite the first rotational direction, activates the double-threaded tube to concurrently (a) withdraw at least some of the fluid into the fluid-retaining chamber from the inflatable balloon of the balloon-based occlusion device, via the catheter fluid-conveyance lumen, and (b) elongate the length of the balloon-based occlusion device by distally moving the actuator, which in turn distally pushes the catheter lumen shaft.

14. The delivery system according to claim 11,
wherein the delivery handle further comprises a plunger pusher and an actuator connected to the catheter lumen shaft, and
wherein the double-threaded tube is shaped so as to define:
a first thread that is threadedly coupled to a corresponding second thread defined by the plunger pusher, and
a third thread that is threadedly coupled to a corresponding fourth thread defined by the actuator.

15. The delivery system according to claim 11,
wherein the delivery handle comprises a safety latch, which is configured to assume locked and unlocked states,
wherein the safety latch, when in the locked state, blocks the double-threaded tube from completion of concurrently (a) expelling at least some of the fluid from the fluid-retaining chamber into the inflatable balloon and (b) shortening the length of the balloon-based implant, and
wherein the safety latch, when in the unlocked state, allows further rotation of the proximal rotatable user-control knob in the first rotation direction to complete concurrently (a) expelling at least some of the fluid from the fluid-retaining chamber into the inflatable balloon and (b) shortening the length of the balloon-based implant.

16. An occlusion system comprising the delivery system according to claim 1, the occlusion system further comprising the balloon-based occlusion device.

17. The occlusion system according to claim 16, wherein the balloon-based occlusion device comprises an actuating shaft, which is (a) disposed at least partially within the balloon, (b) connected to a distal end portion of the balloon, and (c) longitudinally moveable with respect to a proximal end portion of the balloon so as to set a distance between the distal and the proximal end portions of the balloon.

18. The occlusion system according to claim 17, wherein the balloon-based occlusion device further comprises a locking mechanism, which is configured to assume locked and unlocked states, and which is configured, when in the locked state, to maintain, between the distal end portion of the balloon and the proximal end portion of the balloon, the distance set using the actuating shaft.

19. A method for delivering and deploying an implantable balloon-based occlusion device that includes an inflatable balloon, the method comprising, using a delivery system:
filling, with fluid, a fluid-retaining chamber of the delivery system, the fluid-retaining chamber delimited by a tubular barrel having a proximal end, a distal end, and an internal surface, wherein a plunger is slidingly disposed in the fluid-retaining chamber so as to provide a movable membrane;
using a delivery catheter of the delivery system, advancing the implantable balloon-based occlusion device to a desired site in a body of a subject, the delivery catheter including (i) a fluid-conveyance lumen catheter, which is shaped so as to define a catheter fluid-conveyance lumen in fluid communication (a) with the fluid-retaining chamber and (b) with the inflatable balloon of the balloon-based occlusion device when the fluid-conveyance lumen catheter is coupled to the inflatable balloon, and (ii) a catheter lumen shaft, which is in reversible connection with the balloon-based occlusion device, longitudinally slidable with respect to a delivery handle; and
thereafter, rotating a proximal rotatable user-control knob of the delivery handle of the delivery system in a first rotation direction, such that that the delivery system concurrently (a) expels at least some of the fluid from the fluid-retaining chamber into the inflatable balloon of the balloon-based occlusion device, via the catheter fluid-conveyance lumen, and (b) shortens a length of the balloon-based occlusion device by proximally pulling the catheter lumen shaft.

20. The method according to claim 19, further comprising, after rotating the proximal rotatable user-control knob in the first rotation direction, rotating the proximal rotatable user-control knob in a second rotational direction opposite the first rotational direction, such that the delivery system concurrently (a) withdraws at least some of the fluid into the fluid-retaining chamber from the inflatable balloon of the balloon-based occlusion device, via the catheter fluid-conveyance lumen, and (b) elongates the length of the balloon-based occlusion device by distally pushing the catheter lumen shaft.

* * * * *